US009931048B2

(12) United States Patent
Ghosh et al.

(10) Patent No.: US 9,931,048 B2
(45) Date of Patent: Apr. 3, 2018

(54) SYSTEMS, METHODS, AND INTERFACES FOR IDENTIFYING EFFECTIVE ELECTRODES

(71) Applicant: Medtronic, Inc., Minneapolis, MN (US)

(72) Inventors: Subham Ghosh, Blaine, MN (US); Jeffrey Gillberg, Coon Rapids, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

(21) Appl. No.: 14/227,962

(22) Filed: Mar. 27, 2014

(65) Prior Publication Data

US 2014/0323893 A1    Oct. 30, 2014

Related U.S. Application Data

(60) Provisional application No. 61/817,483, filed on Apr. 30, 2013, provisional application No. 61/913,795, filed on Dec. 9, 2013.

(51) Int. Cl.
| | |
|---|---|
| *A61B 5/04* | (2006.01) |
| *A61B 5/044* | (2006.01) |
| *A61N 1/37* | (2006.01) |
| *A61N 1/362* | (2006.01) |
| *A61N 1/372* | (2006.01) |
| *A61N 1/08* | (2006.01) |

(52) U.S. Cl.
CPC .............. *A61B 5/044* (2013.01); *A61N 1/362* (2013.01); *A61N 1/371* (2013.01); *A61N 1/37247* (2013.01); *A61N 2001/083* (2013.01)

(58) Field of Classification Search
CPC ..... A61N 1/3627; A61N 1/3684; A61B 5/044
See application file for complete search history.

(56) References Cited

U.S. PATENT DOCUMENTS

| 4,233,987 A | 11/1980 | Feingold |
| 4,402,323 A | 9/1983 | White |

(Continued)

FOREIGN PATENT DOCUMENTS

| CN | 1043621 A | 11/1990 |
| CN | 1253761 A | 5/2000 |

(Continued)

OTHER PUBLICATIONS

International Search Report and Written Opinion dated Mar. 9, 2015, for International Application No. PCT/US2014/069214.

(Continued)

*Primary Examiner* — Michael D Abreu
(74) *Attorney, Agent, or Firm* — Mueting, Raasch & Gebhardt, P.A.

(57) ABSTRACT

Systems, methods, and interfaces are described herein for identification of effective electrodes to be used in sensing and/or therapy. Two or more portions of a signal monitored using an electrode may be compared to determine whether the electrode is effective. The two or more portions may correspond to the same portion or window of a cardiac cycle. Further, signals from a first electrode and from a second electrode located proximate the first electrode may be compared to determine whether one or both of the electrodes are effective.

20 Claims, 19 Drawing Sheets

(56) References Cited

U.S. PATENT DOCUMENTS

| | | |
|---|---|---|
| 4,428,378 A | 1/1984 | Anderson et al. |
| 4,497,326 A | 2/1985 | Curry |
| 4,566,456 A | 1/1986 | Koning et al. |
| 4,593,702 A | 6/1986 | Kepski |
| 4,674,511 A | 6/1987 | Cartmell |
| 4,763,660 A | 8/1988 | Kroll et al. |
| 4,777,955 A | 10/1988 | Brayten et al. |
| 4,787,389 A | 11/1988 | Tarjan |
| 4,979,507 A | 12/1990 | Heinz et al. |
| 5,052,388 A | 10/1991 | Sivula et al. |
| 5,054,496 A | 10/1991 | Wen et al. |
| 5,311,873 A | 5/1994 | Savard et al. |
| 5,331,960 A | 7/1994 | Lavine |
| 5,334,220 A | 8/1994 | Sholder |
| 5,443,492 A | 8/1995 | Stokes et al. |
| 5,485,849 A | 1/1996 | Panescu et al. |
| 5,514,163 A | 5/1996 | Markowitz et al. |
| 5,552,645 A | 9/1996 | Weng |
| 5,628,778 A | 5/1997 | Kruse et al. |
| 5,671,752 A | 9/1997 | Sinderby et al. |
| 5,683,429 A | 11/1997 | Mehra |
| 5,683,432 A | 11/1997 | Goedeke et al. |
| 5,687,737 A | 11/1997 | Branham et al. |
| 5,810,740 A | 9/1998 | Paisner |
| 5,876,336 A | 3/1999 | Swanson et al. |
| 5,891,045 A | 4/1999 | Albrecht et al. |
| 5,922,014 A | 7/1999 | Warman et al. |
| 6,055,448 A | 4/2000 | Anderson et al. |
| 6,128,535 A | 10/2000 | Maarse et al. |
| 6,141,588 A | 10/2000 | Cox et al. |
| 6,187,032 B1 | 2/2001 | Ohyu et al. |
| 6,205,357 B1 | 3/2001 | Ideker et al. |
| 6,226,542 B1 | 5/2001 | Reisfeld |
| 6,236,883 B1 | 5/2001 | Ciaccio et al. |
| 6,243,603 B1 | 6/2001 | Ideker et al. |
| 6,246,898 B1 | 6/2001 | Vesely et al. |
| 6,301,496 B1 | 10/2001 | Reisfeld |
| 6,311,089 B1 | 10/2001 | Mann et al. |
| 6,330,476 B1 | 12/2001 | Ben-Haim et al. |
| 6,358,214 B1 | 3/2002 | Tereschouk |
| 6,377,856 B1 | 4/2002 | Carson |
| 6,381,493 B1 | 4/2002 | Stadler et al. |
| 6,393,316 B1 | 5/2002 | Gillberg et al. |
| 6,418,346 B1 | 7/2002 | Nelson et al. |
| 6,442,433 B1 | 8/2002 | Linberg |
| 6,456,867 B2 | 9/2002 | Reisfeld |
| 6,473,638 B2 | 10/2002 | Ferek-Petric |
| 6,480,745 B2 | 11/2002 | Nelson et al. |
| 6,484,118 B1 | 11/2002 | Govari |
| 6,507,756 B1 | 1/2003 | Heynen et al. |
| 6,532,379 B2 | 3/2003 | Stratbucker |
| 6,584,343 B1 | 6/2003 | Ransbury et al. |
| 6,599,250 B2 | 7/2003 | Webb et al. |
| 6,625,482 B1 | 9/2003 | Panescu et al. |
| 6,640,136 B1 | 10/2003 | Helland et al. |
| 6,650,927 B1 | 11/2003 | Keidar |
| 6,766,189 B2 | 7/2004 | Yu et al. |
| 6,772,004 B2 | 8/2004 | Rudy |
| 6,804,555 B2 | 10/2004 | Warkentin |
| 6,847,836 B1 | 1/2005 | Sujdak |
| 6,856,830 B2 | 2/2005 | He |
| 6,882,882 B2 | 4/2005 | Struble et al. |
| 6,885,889 B2 | 4/2005 | Chinchoy |
| 6,915,149 B2 | 7/2005 | Ben-Haim |
| 6,968,237 B2 | 11/2005 | Doan et al. |
| 6,975,900 B2 | 12/2005 | Rudy et al. |
| 6,978,184 B1 | 12/2005 | Marcus et al. |
| 6,980,675 B2 | 12/2005 | Evron et al. |
| 7,016,719 B2 | 3/2006 | Rudy et al. |
| 7,031,777 B2 | 4/2006 | Hine et al. |
| 7,058,443 B2 | 6/2006 | Struble |
| 7,062,315 B2 | 6/2006 | Koyrakh et al. |
| 7,092,759 B2 | 8/2006 | Nehls et al. |
| 7,142,922 B2 | 11/2006 | Spinelli et al. |
| 7,184,835 B2 | 2/2007 | Kramer et al. |
| 7,215,998 B2 | 5/2007 | Wesselink et al. |
| 7,286,866 B2 | 10/2007 | Okerlund et al. |
| 7,308,297 B2 | 12/2007 | Reddy et al. |
| 7,308,299 B2 | 12/2007 | Burrell et al. |
| 7,313,444 B2 | 12/2007 | Pianca et al. |
| 7,321,677 B2 | 1/2008 | Evron et al. |
| 7,346,381 B2 | 3/2008 | Okerlund et al. |
| 7,398,116 B2 | 7/2008 | Edwards |
| 7,426,412 B1 | 9/2008 | Schecter |
| 7,454,248 B2 | 11/2008 | Burrell et al. |
| 7,499,743 B2 | 3/2009 | Vass et al. |
| 7,509,170 B2 | 3/2009 | Zhang et al. |
| 7,565,190 B2 | 7/2009 | Okerlund et al. |
| 7,587,074 B2 | 9/2009 | Zarkh et al. |
| 7,599,730 B2 | 10/2009 | Hunter et al. |
| 7,610,088 B2 | 10/2009 | Chinchoy |
| 7,613,500 B2 | 11/2009 | Vass et al. |
| 7,616,993 B2 | 11/2009 | Müssig et al. |
| 7,664,550 B2 | 2/2010 | Eick et al. |
| 7,684,863 B2 | 3/2010 | Parikh et al. |
| 7,742,629 B2 | 6/2010 | Zarkh et al. |
| 7,747,047 B2 | 6/2010 | Okerlund et al. |
| 7,751,882 B1 | 7/2010 | Helland et al. |
| 7,769,451 B2 | 8/2010 | Yang et al. |
| 7,778,685 B2 | 8/2010 | Evron et al. |
| 7,778,686 B2 | 8/2010 | Vass et al. |
| 7,787,951 B1 | 8/2010 | Min |
| 7,813,785 B2 | 10/2010 | Okerlund et al. |
| 7,818,040 B2 | 10/2010 | Spear et al. |
| 7,848,807 B2 | 12/2010 | Wang |
| 7,860,580 B2 | 12/2010 | Falk et al. |
| 7,894,889 B2 | 2/2011 | Zhang |
| 7,912,544 B1 | 3/2011 | Min et al. |
| 7,917,214 B1 | 3/2011 | Gill et al. |
| 7,941,213 B2 | 5/2011 | Markowitz et al. |
| 7,953,475 B2 | 5/2011 | Harlev et al. |
| 7,953,482 B2 | 5/2011 | Hess |
| 7,983,743 B2 | 7/2011 | Rudy et al. |
| 7,996,063 B2 | 8/2011 | Vass et al. |
| 7,996,070 B2 | 8/2011 | van Dam et al. |
| 8,010,194 B2 | 8/2011 | Muller |
| 8,019,402 B1 | 9/2011 | Kryzpow et al. |
| 8,019,409 B2 | 9/2011 | Rosenberg et al. |
| 8,032,229 B2 | 10/2011 | Gerber et al. |
| 8,036,743 B2 | 10/2011 | Savage et al. |
| 8,060,185 B2 | 11/2011 | Hunter et al. |
| 8,150,513 B2 | 4/2012 | Chinchoy |
| 8,160,700 B1 | 4/2012 | Ryu et al. |
| 8,175,703 B2 | 5/2012 | Dong et al. |
| 8,180,428 B2 | 5/2012 | Kaiser et al. |
| 8,195,292 B2 | 6/2012 | Rosenberg et al. |
| 8,213,693 B1 | 7/2012 | Li |
| 8,214,041 B2 | 7/2012 | Van Gelder et al. |
| 8,265,738 B1 | 9/2012 | Min et al. |
| 8,285,377 B2 | 10/2012 | Rosenberg et al. |
| 8,295,943 B2 | 10/2012 | Eggen et al. |
| 8,326,419 B2 | 12/2012 | Rosenberg et al. |
| 8,332,030 B2 | 12/2012 | Hess et al. |
| 8,380,308 B2 | 2/2013 | Rosenberg et al. |
| 8,401,616 B2 | 3/2013 | Verard et al. |
| 8,478,388 B2 | 7/2013 | Nguyen et al. |
| 8,527,051 B1 | 9/2013 | Hedberg et al. |
| 8,583,230 B2 | 11/2013 | Ryu et al. |
| 8,615,298 B2 | 12/2013 | Ghosh et al. |
| 8,617,082 B2 | 12/2013 | Zhang et al. |
| 8,620,433 B2 | 12/2013 | Ghosh et al. |
| 8,639,333 B2 | 1/2014 | Stadler et al. |
| 8,694,099 B2 | 4/2014 | Ghosh et al. |
| 8,738,132 B1 | 5/2014 | Ghosh et al. |
| 8,744,576 B2 | 6/2014 | Munsterman et al. |
| 8,768,465 B2 | 7/2014 | Ghosh et al. |
| 8,805,504 B2 | 8/2014 | Sweeney |
| 8,972,228 B2 | 3/2015 | Ghosh et al. |
| 9,037,238 B2 | 5/2015 | Stadler et al. |
| 9,155,897 B2 | 10/2015 | Ghosh et al. |
| 9,199,087 B2 | 12/2015 | Stadler et al. |
| 9,265,951 B2 | 2/2016 | Sweeney |
| 9,265,954 B2 | 2/2016 | Ghosh |
| 9,265,955 B2 | 2/2016 | Ghosh |

(56) References Cited

U.S. PATENT DOCUMENTS

| | | |
|---|---|---|
| 9,278,219 B2 | 3/2016 | Ghosh |
| 9,278,220 B2 | 3/2016 | Ghosh |
| 9,282,907 B2 | 3/2016 | Ghosh |
| 9,320,446 B2 | 4/2016 | Gillberg et al. |
| 2002/0072682 A1* | 6/2002 | Hopman .............. A61B 5/0006 600/509 |
| 2002/0087089 A1 | 7/2002 | Ben-Haim |
| 2002/0143264 A1 | 10/2002 | Ding et al. |
| 2002/0161307 A1 | 10/2002 | Yu et al. |
| 2002/0169484 A1 | 11/2002 | Mathis et al. |
| 2003/0018277 A1 | 1/2003 | He |
| 2003/0050670 A1 | 3/2003 | Spinelli et al. |
| 2003/0105495 A1 | 6/2003 | Yu et al. |
| 2003/0236466 A1 | 12/2003 | Tarjan et al. |
| 2004/0015081 A1 | 1/2004 | Kramer et al. |
| 2004/0059237 A1* | 3/2004 | Narayan ............ A61B 5/04525 600/509 |
| 2004/0097806 A1 | 5/2004 | Hunter et al. |
| 2004/0102812 A1 | 5/2004 | Yonce et al. |
| 2004/0122479 A1 | 6/2004 | Spinelli et al. |
| 2004/0162496 A1 | 8/2004 | Yu et al. |
| 2004/0172078 A1 | 9/2004 | Chinchoy |
| 2004/0172079 A1 | 9/2004 | Chinchoy |
| 2004/0193223 A1 | 9/2004 | Kramer et al. |
| 2004/0215245 A1 | 10/2004 | Stahmann et al. |
| 2004/0215252 A1 | 10/2004 | Verbeek et al. |
| 2004/0220635 A1 | 11/2004 | Burnes |
| 2004/0267321 A1 | 12/2004 | Boileau et al. |
| 2005/0008210 A1 | 1/2005 | Evron et al. |
| 2005/0027320 A1 | 2/2005 | Nehls et al. |
| 2005/0090870 A1 | 4/2005 | Hine et al. |
| 2005/0096522 A1 | 5/2005 | Reddy et al. |
| 2005/0149138 A1 | 7/2005 | Min et al. |
| 2006/0074285 A1 | 4/2006 | Zarkh et al. |
| 2006/0224198 A1 | 10/2006 | Dong et al. |
| 2006/0235478 A1 | 10/2006 | Van Gelder et al. |
| 2006/0253162 A1 | 11/2006 | Zhang et al. |
| 2007/0142871 A1 | 6/2007 | Libbus et al. |
| 2007/0232943 A1 | 10/2007 | Harel et al. |
| 2007/0250129 A1 | 10/2007 | Van Oort |
| 2007/0265508 A1 | 11/2007 | Sheikhzadeh-Nadjar et al. |
| 2008/0021336 A1 | 1/2008 | Dobak et al. |
| 2008/0058656 A1* | 3/2008 | Costello ............... A61B 5/1107 600/508 |
| 2008/0119903 A1 | 5/2008 | Arcot-Krishnamurthy et al. |
| 2008/0140143 A1 | 6/2008 | Ettori et al. |
| 2008/0146954 A1 | 6/2008 | Bojovic et al. |
| 2008/0242976 A1 | 10/2008 | Robertson et al. |
| 2008/0269818 A1 | 10/2008 | Sullivan et al. |
| 2008/0269823 A1 | 10/2008 | Burnes et al. |
| 2008/0281195 A1 | 11/2008 | Heimdal |
| 2008/0306567 A1 | 12/2008 | Park et al. |
| 2008/0306568 A1 | 12/2008 | Ding et al. |
| 2009/0005832 A1 | 1/2009 | Zhu et al. |
| 2009/0036947 A1 | 2/2009 | Westlund et al. |
| 2009/0043352 A1 | 2/2009 | Brooke et al. |
| 2009/0048528 A1 | 2/2009 | Hopenfeld et al. |
| 2009/0053102 A2 | 2/2009 | Rudy et al. |
| 2009/0054941 A1 | 2/2009 | Eggen et al. |
| 2009/0054946 A1 | 2/2009 | Sommer et al. |
| 2009/0084382 A1 | 4/2009 | Jalde et al. |
| 2009/0093857 A1 | 4/2009 | Markowitz et al. |
| 2009/0099468 A1 | 4/2009 | Thiagalingam et al. |
| 2009/0099469 A1 | 4/2009 | Flores |
| 2009/0099619 A1 | 4/2009 | Lessmeier et al. |
| 2009/0112109 A1 | 4/2009 | Kuklik et al. |
| 2009/0143838 A1 | 6/2009 | Libbus et al. |
| 2009/0157134 A1 | 6/2009 | Ziglio et al. |
| 2009/0157136 A1 | 6/2009 | Yang et al. |
| 2009/0198298 A1 | 8/2009 | Kaiser et al. |
| 2009/0216112 A1 | 8/2009 | Assis et al. |
| 2009/0232448 A1 | 9/2009 | Barmash et al. |
| 2009/0234414 A1 | 9/2009 | Sambelashvili et al. |
| 2009/0254140 A1 | 10/2009 | Rosenberg et al. |
| 2009/0270729 A1 | 10/2009 | Corbucci et al. |
| 2009/0270937 A1 | 10/2009 | Yonce et al. |
| 2009/0299201 A1 | 12/2009 | Gunderson |
| 2009/0299423 A1 | 12/2009 | Min |
| 2009/0306732 A1 | 12/2009 | Rosenberg et al. |
| 2009/0318995 A1 | 12/2009 | Keel et al. |
| 2010/0022873 A1 | 1/2010 | Hunter et al. |
| 2010/0049063 A1 | 2/2010 | Dobak, III |
| 2010/0069987 A1 | 3/2010 | Min et al. |
| 2010/0087888 A1 | 4/2010 | Maskara |
| 2010/0094149 A1 | 4/2010 | Kohut et al. |
| 2010/0113954 A1 | 5/2010 | Zhou |
| 2010/0114229 A1 | 5/2010 | Chinchoy |
| 2010/0121403 A1 | 5/2010 | Schecter et al. |
| 2010/0145405 A1 | 6/2010 | Min et al. |
| 2010/0174137 A1 | 7/2010 | Shim |
| 2010/0198292 A1 | 8/2010 | Honeck et al. |
| 2010/0228138 A1 | 9/2010 | Chen |
| 2010/0234916 A1 | 9/2010 | Turcott et al. |
| 2010/0254583 A1 | 10/2010 | Chan et al. |
| 2010/0268059 A1 | 10/2010 | Ryu et al. |
| 2011/0004111 A1 | 1/2011 | Gill et al. |
| 2011/0004264 A1 | 1/2011 | Siejko et al. |
| 2011/0022112 A1 | 1/2011 | Min |
| 2011/0054286 A1 | 3/2011 | Crosby |
| 2011/0054559 A1 | 3/2011 | Rosenberg et al. |
| 2011/0054560 A1 | 3/2011 | Rosenberg et al. |
| 2011/0075896 A1 | 3/2011 | Matsumoto |
| 2011/0092809 A1 | 4/2011 | Nguyen et al. |
| 2011/0112398 A1 | 5/2011 | Zarkh et al. |
| 2011/0118803 A1 | 5/2011 | Hou et al. |
| 2011/0137369 A1 | 6/2011 | Ryu et al. |
| 2011/0144510 A1 | 6/2011 | Ryu et al. |
| 2011/0172728 A1 | 7/2011 | Wang |
| 2011/0190615 A1 | 8/2011 | Phillips et al. |
| 2011/0201915 A1 | 8/2011 | Gogin et al. |
| 2011/0213260 A1 | 9/2011 | Keel et al. |
| 2011/0319954 A1 | 12/2011 | Niazi et al. |
| 2012/0004567 A1 | 1/2012 | Eberle et al. |
| 2012/0101543 A1 | 4/2012 | Demmer et al. |
| 2012/0101546 A1 | 4/2012 | Stadler et al. |
| 2012/0203090 A1 | 8/2012 | Min |
| 2012/0253419 A1 | 10/2012 | Rosenberg et al. |
| 2012/0283587 A1 | 11/2012 | Ghosh et al. |
| 2012/0284003 A1 | 11/2012 | Ghosh et al. |
| 2012/0296387 A1 | 11/2012 | Zhang et al. |
| 2012/0296388 A1 | 11/2012 | Zhang et al. |
| 2012/0302904 A1 | 11/2012 | Lian et al. |
| 2012/0303084 A1 | 11/2012 | Kleckner et al. |
| 2012/0310297 A1 | 12/2012 | Sweeney |
| 2012/0330179 A1 | 12/2012 | Yuk et al. |
| 2013/0006332 A1 | 1/2013 | Sommer et al. |
| 2013/0018250 A1 | 1/2013 | Caprio et al. |
| 2013/0018251 A1 | 1/2013 | Caprio et al. |
| 2013/0030491 A1 | 1/2013 | Stadler et al. |
| 2013/0060298 A1 | 3/2013 | Splett et al. |
| 2013/0072790 A1 | 3/2013 | Ludwig et al. |
| 2013/0096446 A1 | 4/2013 | Michael et al. |
| 2013/0116739 A1 | 5/2013 | Brada et al. |
| 2013/0131529 A1 | 5/2013 | Jia et al. |
| 2013/0131749 A1 | 5/2013 | Sheldon et al. |
| 2013/0131751 A1 | 5/2013 | Stadler et al. |
| 2013/0136035 A1 | 5/2013 | Bange et al. |
| 2013/0150913 A1* | 6/2013 | Bornzin ............... A61N 1/3706 607/28 |
| 2013/0165983 A1 | 6/2013 | Ghosh et al. |
| 2013/0165988 A1 | 6/2013 | Ghosh |
| 2013/0261471 A1 | 10/2013 | Saha et al. |
| 2013/0261688 A1 | 10/2013 | Dong et al. |
| 2013/0289640 A1 | 10/2013 | Zhang et al. |
| 2013/0296726 A1 | 11/2013 | Niebauer et al. |
| 2013/0304407 A1 | 11/2013 | George et al. |
| 2013/0324828 A1 | 12/2013 | Nishiwaki et al. |
| 2014/0005563 A1 | 1/2014 | Ramanathan et al. |
| 2014/0018872 A1 | 1/2014 | Siejko et al. |
| 2014/0135866 A1 | 5/2014 | Ramanathan et al. |
| 2014/0135867 A1 | 5/2014 | Demmer et al. |
| 2014/0163633 A1 | 6/2014 | Ghosh et al. |
| 2014/0222099 A1 | 8/2014 | Sweeney |
| 2014/0236252 A1 | 8/2014 | Ghosh et al. |

(56) References Cited

U.S. PATENT DOCUMENTS

| | | |
|---|---|---|
| 2014/0276125 A1 | 9/2014 | Hou et al. |
| 2014/0277233 A1 | 9/2014 | Ghosh |
| 2014/0323882 A1 | 10/2014 | Ghosh et al. |
| 2014/0323892 A1 | 10/2014 | Ghosh et al. |
| 2014/0371807 A1 | 12/2014 | Ghosh et al. |
| 2014/0371808 A1 | 12/2014 | Ghosh et al. |
| 2014/0371832 A1 | 12/2014 | Ghosh et al. |
| 2014/0371833 A1 | 12/2014 | Ghosh et al. |
| 2015/0032016 A1 | 1/2015 | Ghosh |
| 2015/0032171 A1 | 1/2015 | Ghosh |
| 2015/0032172 A1 | 1/2015 | Ghosh |
| 2015/0032173 A1 | 1/2015 | Ghosh |
| 2015/0045849 A1 | 2/2015 | Ghosh et al. |
| 2015/0142069 A1 | 5/2015 | Sambelashvili |
| 2015/0157225 A1 | 6/2015 | Gillberg et al. |
| 2015/0157231 A1 | 6/2015 | Gillberg et al. |
| 2015/0157232 A1 | 6/2015 | Gillberg et al. |
| 2015/0157865 A1 | 6/2015 | Gillberg et al. |
| 2015/0216434 A1 | 8/2015 | Ghosh et al. |
| 2015/0265840 A1 | 9/2015 | Ghosh et al. |
| 2016/0030747 A1 | 2/2016 | Thakur et al. |
| 2016/0030751 A1 | 2/2016 | Ghosh et al. |
| 2016/0045737 A1 | 2/2016 | Ghosh et al. |
| 2016/0045738 A1 | 2/2016 | Ghosh et al. |
| 2016/0045744 A1 | 2/2016 | Ghosh et al. |
| 2016/0184590 A1 | 6/2016 | Gosh |

FOREIGN PATENT DOCUMENTS

| | | |
|---|---|---|
| CN | 1878595 A | 12/2006 |
| CN | 101073502 A | 11/2007 |
| EP | 1 072 284 A2 | 1/2001 |
| EP | 1 504 713 A1 | 2/2005 |
| EP | 2 016 976 A1 | 1/2009 |
| EP | 2 391 270 A1 | 7/2011 |
| EP | 1 925 337 B1 | 3/2012 |
| EP | 2 436 309 A2 | 4/2012 |
| EP | 2 435 132 B1 | 8/2013 |
| WO | WO 98/26712 A1 | 6/1998 |
| WO | WO 1999/006112 A1 | 2/1999 |
| WO | WO 00/45700 | 8/2000 |
| WO | WO 01/67950 A1 | 9/2001 |
| WO | WO 2003/070323 A1 | 8/2003 |
| WO | WO 2005/056108 A2 | 6/2005 |
| WO | WO 2006/069215 A2 | 6/2006 |
| WO | WO 2006/105474 A2 | 10/2006 |
| WO | WO 2006/115777 A1 | 11/2006 |
| WO | WO 2006/117773 A1 | 11/2006 |
| WO | WO 2007/013994 A2 | 2/2007 |
| WO | WO 2007/027940 A2 | 3/2007 |
| WO | WO 2007/013994 A3 | 4/2007 |
| WO | WO 2007/027940 A3 | 6/2007 |
| WO | WO 2007/139456 A1 | 12/2007 |
| WO | WO 2008/151077 A2 | 12/2008 |
| WO | WO 2006/069215 A3 | 6/2009 |
| WO | WO 2009/079344 A1 | 6/2009 |
| WO | WO 2009/139911 A2 | 11/2009 |
| WO | WO 2009/148429 A1 | 12/2009 |
| WO | WO 2010/019494 A1 | 2/2010 |
| WO | WO 2010/071520 A1 | 6/2010 |
| WO | WO 2010/088040 A1 | 8/2010 |
| WO | WO 2010/088485 A1 | 8/2010 |
| WO | WO 2011/070166 A1 | 6/2011 |
| WO | WO 2011/090622 A1 | 7/2011 |
| WO | WO 2011/099992 A1 | 8/2011 |
| WO | WO 2012/037471 A2 | 3/2012 |
| WO | WO 2012/037471 A3 | 6/2012 |
| WO | WO 2012/106297 A2 | 8/2012 |
| WO | WO 2012/106297 A3 | 8/2012 |
| WO | WO 2012/109618 A2 | 8/2012 |
| WO | WO 2012/110940 A1 | 8/2012 |
| WO | WO 2012/109618 A3 | 11/2012 |
| WO | WO 2012/151364 A1 | 11/2012 |
| WO | WO 2012/151389 A1 | 11/2012 |
| WO | WO 2013/006724 A2 | 1/2013 |
| WO | WO 2013/010165 A1 | 1/2013 |
| WO | WO 2013/010184 A1 | 1/2013 |
| WO | WO 2013/006724 A3 | 4/2013 |
| WO | PCT/US2014/036153 | 4/2014 |
| WO | PCT/US2014/036163 | 4/2014 |
| WO | WO 2014/179454 A1 | 11/2014 |
| WO | WO 2014/179459 A2 | 11/2014 |
| WO | WO 2014/179459 A3 | 1/2015 |
| WO | WO 2015/013271 A1 | 1/2015 |
| WO | WO 2015/013493 A1 | 1/2015 |
| WO | WO 2015/013574 A1 | 1/2015 |

OTHER PUBLICATIONS

International Search Report and Written Opinion dated Mar. 17, 2015, for International Application No. PCT/US2014/069192.
International Search Report and Written Opinion dated Mar. 16, 2015, for International Application No. PCT/US2014/069182.
U.S. Appl. No. 14/173,288, filed Feb. 5, 2014, Sambelashvili.
Biffi et al., "Occurrence of Phrenic Nerve Stimulation in Cardiac Resynchronization Therapy Patients: the Role of Left Ventricular Lead Type and Placement Site," *Europace*, 2013; 15:77-82.
Hayes et al., "Cardiac Resynchronization Therapy and the Relationship of Percent Biventricular Pacing to Symptoms and Survival," *Heart Rhythm*, Sep. 2011; 8(9):1469-1475.
Singh et al., "Left Ventricular Lead Position and Clinical Outcome in the Multicenter Automatic Defibrillator Implantation Trial-Cardiac Resynchronization Therapy (MADIT-CRT) Trial," *Circulation*, 2011; 123:1159-1166.
Vardas et al., The Task Force for Cardiac Pacing and Cardiac Resynchronization Therapy of the European Society of Cardiology. Developed in Collaboration with the European Heart Rhythm Association, *European Heart Journal*, 2007; 28:2256-2295.
International Search Report and Written Opinion dated May 3, 2012 for International Application No. PCT/US2012/036262; 9 pages.
International Search Report and Written Opinion dated May 3, 2012 for International Application No. PCT/US2012/036302; 9 pages.
International Search Report and Written Opinion dated Apr. 8, 2015, for International Application No. PCT/US2014/069070; 11 pages.
International Search Report and Written Opinion dated Jun. 11, 2015 for International Application No. PCT/US2015/021442; 13 pages.
International Search Report / Written Opinion, dated Aug. 6, 2014; Patent Application No. PCT/US2014/036153, filed Apr. 30, 2014; 14 pages.
International Search Report / Written Opinion, dated Nov. 7, 2014; Patent Application No. PCT/US2014/036163, filed Apr. 30, 2014; 12 pages.
International Search Report / Written Opinion, dated Oct. 28, 2014; Patent Application No. PCT/US2014/041928, filed Jun. 11, 2014; 15 pages.
International Search Report / Written Opinion, dated Oct. 24, 2014; Patent Application No. PCT/US2014/041929, filed Jun. 11, 2014; 15 pages.
International Search Report and Written Opinion for PCT/US2014/0247583, dated Nov. 4, 2014; 7 pages.
International Search Report and Written Opinion dated Nov. 12, 2014 for International Application No. PCT/US2014/047971; 7 pages.
International Search Report and Written Opinion dated Nov. 12, 2014 for International Application No. PCT/US2014/048120; 7 pages.
Cuculich et al., "The Electrophysiological Cardiac Ventricular Substrate in Patients After Myocardial Infection," *J. Am. Coll. Cardiol.*, 2011; 58:1893-1902.
Dawoud et al., "Inverse Electrocardiographic Imaging to Assess Electrical Dyssynchrony in Cardiac Resynchronization Therapy Patients," *Computing in Cardiology*, 2012; 39:993-996.
Ghosh et al., "Electrophysiological Substrate and Intraventricular LV Dyssynchrony in Non-ischemic Heart Failure Patients Undergoing Cardiac Resynchronization Therapy," *Heart rhythm : the official journal of the Heart Rhythm Society*, 2011; 8(5):692-699.

(56) References Cited

OTHER PUBLICATIONS

Medtronic Vitatron Carelink Encore® Programmer Model 29901 Reference Manual, 2013, Medtronic, Inc., Minneapolis, MN.
Potse et al., "Mathematical Modeling and Simulation of Ventricular Activation Sequences: Implications for Cardiac Resynchronization Therapy," *J. of Cardiovasc. Trans. Res.*, 2012; 5:146-158.
Prinzen et al., "Cardiac Resynchronization Therapy State-of-the-Art of Current Applications, Guidelines, Ongoing Trials, and Areas of Controversy" *Circulation*, 2013; 128: 2407-2418.
Strik et al., "Electrical and Mechanical Ventricular Activation During Left Bundle Branch Block and Resynchronization," *J. of Cardiovasc. Trans. Res.*, 2012; 5:11-126.
U.S. Appl. No. 13/916,353, filed Jun. 12, 2013, Ghosh.
U.S. Appl. No. 13/916,377, filed Jun. 12, 2013, Ghosh.
U.S. Appl. No. 13/952,043, filed Jul. 26, 2013, Ghosh.
U.S. Appl. No. 13/952,061, filed Jul. 26, 2013, Ghosh.
U.S. Appl. No. 14/190,508, filed Feb. 26, 2014.
U.S. Appl. No. 14/190,578, filed Feb. 26, 2014.
U.S. Appl. No. 14/220,733, filed Mar. 20, 2014, Ghosh et al.
U.S. Appl. No. 14/227,719, filed Mar. 27, 2014, Gillberg et al.
U.S. Appl. No. 14/227,919, filed Mar. 27, 2014, Ghosh et al.
U.S. Appl. No. 14/227,955, filed Mar. 27, 2014, Ghosh et al.
U.S. Appl. No. 14/227,962, filed Mar. 27, 2014, Ghosh et al.
U.S. Appl. No. 14/228,009, filed Mar. 27, 2014, Gillberg et al.
U.S. Appl. No. 14/228,024, filed Mar. 27, 2014, Ghosh et al.
U.S. Appl. No. 14/228,038, filed Mar. 27, 2014, Ghosh et al.
International Search Report and Written Opinion for PCT/US2014/036262, dated May 3, 2012; 9 pg.
International Search Report and Written Opinion for PCT/US2014/036302, dated May 3, 2012; 9 pg.
"CardioGuide System Enables Real-Time Navigation of Left Ventricular Leads During Medtronic CRT Implants," Press Release, Apr. 9, 2013, Medtronic, Inc., 2 pgs.
Czerwinska et al., "Method of Segmentation of Thorax Organs Images Applied to Modeling the Cardiac Electrical Field," *Engineering in Medicine and Biology Society*, Proceedings of the $22^{nd}$ Annual International Conference of the IEEE, vol. 1, 23, Jul. 23, 2000.; pp. 402-405.
Ghosh et al. "Accuracy of Quadratic Versus Linear Interpolation in Noninvasive Electrocardiographic Imaging (ECGI)," *Annuals of Biomedical Engineering*, vol. 33, No. 9. Sep. 2005; pp. 1187-1201.
Ghosh et al., "Cardiac Memory in Patents with Wolff-Parkinson-White Syndrome: Noninvasive Imaging of Activation and Repolarization Before and After Catheter Ablation" *Circulation*, 2008; 118:907-915. Published online Aug. 12, 2008.
Ghosh et al. "Application of L1-Norm Regularization to Epicardial Potential Solution of the Inverse Electrocardiography Problem," *Annuals of Biomedical Engineering*, vol. 37, No. 5, May 2009; pp. 902-912.
Gold et al., "Comparison of Stimulation Sites within Left Ventricular Veins on the Acute Hemodynamic Effects of Cardiac Resynchronization Therapy" *Heart Rhythm*, Apr. 2005; 2(4):376-381.
Gulrajani, "The Forward and Inverse Problems of Electrocardiography," *IEEE Engineering in Medicine and Biology*, IEEE Service Center, vol. 17, No. 5, Sep. 1, 1988; pp. 84-101, 122.
Hansen, "Regularization Tools: a Matlab Package for Analysis and Solution of Discrete Ill-Posed Problems," Version 4.1 for Matlab 7.3; Mar. 2008; 128 pages. Retrieved from the Internet: Jun. 19, 2014 http://www.mathworks.com/matlabcentral/fileexchange/52-regtools.
"Heart Failure Management" datasheet [online]. Medtronic, Minneapolis, Minnesota, [Last updated on Jun. 3, 2013].Retrieved from the Internet: www.medtronic.com; 9 pages.
Jia et al., "Electrocardiographic Imaging of Cardiac Resynchronization Therapy in Heart Failure: Observation of Variable Electrophysiologic Responses," *Heart Rhythm*, vol. 3, No. 3; Mar. 1, 2006, pp. 296-310.

Kornreich, "Body Surface Potential Mapping of ST Segment Changes in Acute Myocardial Infarction," *Circulation*, 1993; 87: 773-782.
Modre et al., "Noninvasive Myocardial Activation Time Imaging: A Novel Inverse Algorithm Applied to Clinical ECG Mapping Data" *IEEE Transactions on Biomedical Engineering*, vol. 49; No. 10, Oct. 2002; pp. 1153-1161.
Ryu et al., "Simultaneous Electrical and Mechanical Mapping Using 3D Cardiac Mapping System: Novel Approach for Optimal Cardiac Resynchronization Therapy," *Journal of Cardiovascular Electrophysiology*, Feb. 2010; 21(2):219-22.
Silva et al., "Cardiac Resynchronization Therapy in Pediatric Congenital Heart Disease: Insights from Noninvasive Electrocardiographic Imaging" *Heart Rhythm*, vol. 6, No. 8. Aug. 1, 2009; pp. 1178-1185.
Sperzel et al., "Intraoperative Characterization of Interventricular Mechanical Dyssynchrony Using Electroanatomic Mapping System—A Feasibility Study," *Journal of Interventional Cardiac Electrophysiology*, Nov. 2012; 35(2):189-96.
Steinhaus BM., "Estimating cardiac transmembrane activation and recovery times from unipolar and bipolar extracellular electrograms : a simulation study," Circulation Research, 1989, 64:449-462.
Sweeney et al., "Analysis of Ventricular Activation Using Surface Electrocardiography to Predict Left Ventricular Reverse Volumetric Remoldeling During Cardiac Resynchronization Therapy," *Circulation*, Feb. 9, 2010; 121(5):626-34. Available online Jan. 25, 2010.
Turner et al, "Electrical and Mechanical Components of Dyssynchrony in Heart Failure Patients with Normal QRS Duration and Left Bundle-Branch Block," *Circulation* 2004; 109: 2544-2549.
Van Deursen et al., "Vectorcardiography as a Tool for Wasy Optimization of Cardiac Resynchronization Therapy in Canine LBBB Hearts," *Circulation Arrhythmia and Electrophysiology*, Jun. 1, 2012; 5(3):544-52. Available online Apr. 24, 2012.
Varma et al., "Placebo CRT," *Journal of Cardiovascular Electrophysiology*, vol. 19, Aug. 2008; p. 878.
Williams et al., "Short-Term Hemodynamic Effects of Cardiac Resynchronization Therapy in Patients With Heart Failure, a Narrow QRS Duration, and No Dyssynchrony," *Circulation*, Oct. 27, 2009; 120: 1687-1694.
Miri et al., "Applicability of body surface potential map in computerized optimization of biventricular pacing," *Annals of Biomedical Engineering*, vol. 38, No. 3, Mar. 2010, pp. 865-875.
Miri et al., "Comparison of the electrophysiologically based optimization methods with different pacing parameters in patient undergoing resynchronization treatment," $30^{th}$ *Annual International IEEE EMBS Conference*, Aug. 2008, pp. 1741-1744.
Miri et al., "Computerized Optimization of Biventricular Pacing Using Body Surface Potential Map," $31^{st}$ *Annual International Conference of the IEEE EMBS*, Sep. 2009, pp. 2815-2818.
Miri et al., "Efficiency of Timing Delays and Electrode Positions in Optimization of Biventricular Pacing: A Simulation Study," *IEEE Transactions on Biomedical Engineering*, Nov. 2009, pp. 2573-2582.
Svendsen et al., "Computational Models of Cardiac Electrical Activation," Chapter 5, Computational Nov. 2010, pp. 73-88.
Wang et al., "Application of the Method of Fundamental Solutions to Potential-based Inverse Electrocardiography," *Annals of Biomedical Engineering*, Aug. 2006, pp. 1272-1288.
Botker MD, PhD., et al., "Electromechanical Mapping for Detection of Myocardial Viability in Patients with ischemia Cardiomyopathy," Circulation, Mar. 2001; vol. 103, No. 12, pp. 1631-1637.
Fung et al., Chapter 20, Optimization of Cardiac Resynchronization Therapy, Cardiac Resynchronization Therapy, Second Edition, Copyright 2008, Blackwell Publishing Ltd., pp. 356-373.
Hopenfeld et al., "The Effect of Conductivity on ST-Segment Epicardial Potentials Arising from Subendocardial Ischemia," Annals of Biomedical Eng., Jun. 2005; vol. 33, No. 6, pp. 751-763.
Nash et al., "An Experimental-Computational Framework for Validating in-vivo ECG Inverse Algorithms," International Journal of Bioelectromagnetism, vol. 2, No. 2, Dec. 31, 2000, 9 pp.
Sweeney et al, QRS Fusion Complex Analysis Using Wave Interference to Predict Reverse Remodeling During Cardiac Resynchronization Therapy, heart Rhythm, 2014, 11:806-813.

(56) References Cited

OTHER PUBLICATIONS

Wellens, MD et al., "The Electrocardiogram 102 Years After Einthoven," Circulation, Feb. 2004; vol. 109, No. 5, pp. 562-564.

* cited by examiner

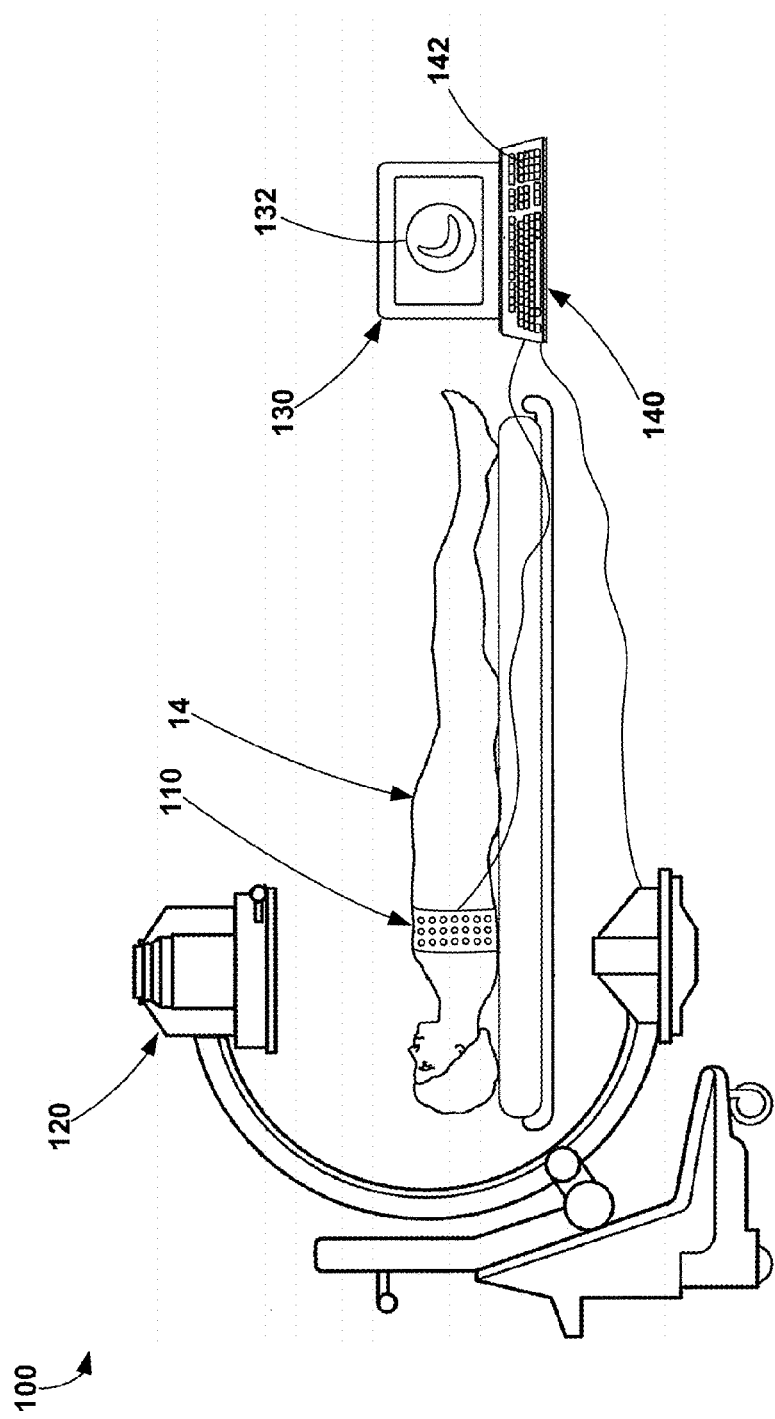

SYSTEMS, METHODS, AND INTERFACES FOR IDENTIFYING EFFECTIVE ELECTRODES

CROSS-REFERENCE TO RELATED APPLICATION

This application claims the benefit of U.S. Provisional Patent Application 61/913,795 entitled "Systems, Methods, and Interfaces for Identifying Effective Electrodes" and filed on Dec. 9, 2013 and U.S. Provisional Patent Application 61/817,483 entitled "Identifying Effective Electrodes" and filed on Apr. 30, 2013, each of which is incorporated herein by reference in its entirety.

BACKGROUND

The disclosure herein relates to systems, methods, and interfaces for identifying effective electrodes used to sense signals from tissue and/or deliver therapy to tissue. The identified electrodes may be used in systems, methods, and interfaces for navigating an implantable electrode to a region of a patient's heart for cardiac therapy.

Electrodes may be used in various systems, devices, and methods for medical treatment of a patient. More specifically, electrodes may be located adjacent, or in contact, with tissue (e.g., skin, cardiac tissue, etc.) of a patient to sense signals from the tissue of the patient and/or deliver therapy to the tissue of the patient. Each of the electrodes may be effective or ineffective for sensing signals from the tissue of the patient and/or delivering therapy to the tissue of the patient for multiple reasons. For example, an electrode may not be effectively coupled to, or in contact with, the tissue of the patient rendering the electrode ineffective for sensing signals form the tissue of the patient and/or delivering therapy to the tissue of the patient. Further, for example, an electrode, or an electrical connection between the electrode and monitoring apparatus, may be damaged or otherwise non-functional rendering the electrode ineffective for sensing signals from the tissue of the patient and/or delivering therapy to the tissue of the patient.

Exemplary apparatus that utilize multiple electrodes may include multipolar catheters (e.g., catheters including multiple electrodes, etc.) configured to record activation times/voltage mapping simultaneously at different points along a coronary sinus vein or some other anatomic structure (e.g., used for electrical mapping). Further, exemplary apparatus may include multi-electrode electrocardiogram (ECG) systems for body-surface potential mapping configured to record simultaneous ECG measurements from multiple electrodes.

SUMMARY

The exemplary systems, apparatus, and methods described herein may be configured to analyze one or more signals from one or more electrodes and evaluate the one or more signals to determine whether the one or more electrodes are effective for sensing signals and/or delivering therapy.

An exemplary system for identifying effective electrodes may include electrode apparatus and computing apparatus. The electrode apparatus may include a plurality of electrodes (e.g., surface electrodes positioned in an array) configured to be located proximate tissue of a patient. The computing apparatus may be coupled to the electrode apparatus for sensing electrical activity using the electrode apparatus and may be configured to perform an effectiveness test for each electrode of the plurality of electrodes resulting in an effectiveness value (e.g., a Pearson correlation coefficient) for each electrode. To perform the effectiveness test for each electrode, the computing apparatus may be further configured to monitor a signal from the patient using an electrode, store a portion of the signal over a preset time period (e.g., less than or equal to 250 milliseconds) for each cardiac cycle of at least two cardiac cycles (e.g. storing the portion of the signal based on a recurring fiducial element within a cardiac signal), where each portion corresponds to the same time frame within each cardiac cycle, and compare at least two stored portions of the signal to provide the effectiveness value representative of the effectiveness of the electrode for sensing signals from the tissue of the patient.

An exemplary method for identifying effective electrodes in a plurality of electrodes (e.g., surface electrodes positioned in an array) located proximate tissue of a patient may include monitoring a signal from the patient using an electrode, storing a portion of the signal over a preset time period (e.g., less than or equal to 250 milliseconds) for each cardiac cycle of at least two cardiac cycles (e.g. storing the portion of the signal based on a recurring fiducial element within a cardiac signal), where each portion corresponds to the same time frame within each cardiac cycle, and comparing at least two stored portions of the signal to provide an effectiveness value (e.g., a Pearson correlation coefficient) representative of the effectiveness of the electrode for sensing signals from the tissue of the patient.

An exemplary system for identifying effective electrodes may include electrode means for monitoring a signal from the patient and computing means for storing a portion of the signal over a preset time period for each cardiac cycle of at least two cardiac cycles. Each portion may correspond to the same time frame within each cardiac cycle. The computing means may be further for comparing at least two stored portions of the signal to provide an effectiveness value representative of the effectiveness of the electrode for sensing signals from the tissue of the patient.

An exemplary system for use in cardiac therapy may include electrode apparatus (e.g., a plurality of electrodes configured to be located proximate tissue of a patient), display apparatus including a graphical user interface (e.g., the graphical user interface may be configured to present information for use in assisting a user in at least one of assessing a patient's cardiac health, evaluating adjusting cardiac therapy delivered to a patient, and navigating at least one implantable electrode to a region of the patient's heart (e.g., graphically depict at least a portion of anatomy, such as blood vessel anatomy, of the patient's heart for use in assisting a user in navigating at least one implantable electrode to a region of the patient's heart, etc.), and computing apparatus coupled to the electrode apparatus and display apparatus. The computing apparatus may be configured to perform an effectiveness test for each electrode of the plurality of electrodes resulting in an effectiveness value for each electrode. To perform the effectiveness test for each electrode, the computing apparatus may be further configured to monitor a signal from the patient using an electrode and store a portion of the signal over a preset time period for each cardiac cycle of at least two cardiac cycles. Each portion may correspond to the same time frame within each cardiac cycle. The computing apparatus may be further configured to compare at least two stored portions of the signal to provide the effectiveness value representative of the effectiveness of the electrode for sensing signals from the tissue of the patient. The computing apparatus may be further configured to display, on the graphical user interface, information for use in assisting a user in at least one of assessing a patient's cardiac health, evaluating and adjusting cardiac therapy delivered to a patient, and navigating at least one implantable electrode to a region of the patient's heart (e.g., at least a portion of anatomy, such as blood vessel anatomy, of the patient's heart for use in assisting a user in navigating at least one implantable electrode to a region of the patient's heart, etc.).

An exemplary method for use in cardiac therapy may include monitoring a signal from the patient using an electrode and storing a portion of the signal over a preset time period for each cardiac cycle of at least two cardiac cycles, each portion corresponds to the same time frame within each cardiac cycle. The exemplary method may further include comparing at least two stored portions of the signal to provide an effectiveness value representative of the effectiveness of the electrode for sensing signals from the tissue of the patient and displaying, on a graphical user interface, information for use in assisting a user in at least one of assessing a patient's cardiac health, evaluating and adjusting cardiac therapy delivered to a patient, and navigating at least one implantable electrode to a region of the patient's heart (e.g., at least a portion of anatomy of the patient's heart for use in assisting a user in navigating at least one implantable electrode to a region of the patient's heart, etc.).

An exemplary system for use in cardiac therapy may include electrode means for monitoring a signal from the patient and computing means for storing a portion of the signal over a preset time period for each cardiac cycle of at least two cardiac cycles. Each portion may correspond to the same time frame within each cardiac cycle. The computing means may be further for comparing at least two stored portions of the signal to provide an effectiveness value representative of the effectiveness of the electrode for sensing signals from the tissue of the patient. The exemplary system may further include display means for displaying, on a graphical user interface, information for use in assisting a user in at least one of assessing a patient's cardiac health, evaluating and adjusting cardiac therapy delivered to a patient, and navigating at least one implantable electrode to a region of the patient's heart (e.g., at least a portion of anatomy, such as blood vessel anatomy, of the patient's heart for use in assisting a user in navigating at least one implantable electrode to a region of the patient's heart, etc.).

In one or more embodiments, the effectiveness value may include a correlation value, the computing apparatus may be further configured to execute or the method may further include disabling any electrode of the plurality of electrodes having a correlation value less than a selected threshold value (e.g., greater than or equal to 0.7 and less than or equal to about 0.95). In one or more embodiments, the effectiveness value may include a correlation value, the computing apparatus may be further configured to execute or the method may further include enabling any electrode of the plurality of electrodes having a correlation value greater than or equal to a selected threshold value.

In one or more embodiments, the computing apparatus may be further configured to execute or the method may further include performing an additional effectiveness test for each electrode of the plurality of electrodes resulting in another correlation value for each electrode if more than a selected percentage of the plurality of electrodes had a correlation value less than a selected threshold value. In one or more embodiments, the computing apparatus may be further configured to execute or the method may further include aligning the at least two portions of the signal prior to the comparison.

One exemplary system for identifying effective electrodes may include electrode apparatus and computing apparatus. The electrode apparatus may include a plurality of electrodes (e.g., surface electrodes positioned in an array) configured to be located proximate tissue of a patient. The computing apparatus may be coupled to the electrode apparatus for sensing electrical activity using the electrode apparatus and may be configured to perform an effectiveness test for each electrode of the plurality of electrodes resulting in an effectiveness value (e.g., representing a correlation value between the primary electrode and one neighbor electrode, a Pearson correlation coefficient, etc.) for each electrode. To perform the effectiveness test for each electrode, the computing apparatus may be further configured to monitor a first signal from the patient using a primary electrode and monitor at least one secondary signal from the patient using at least one neighbor electrode. At least one neighbor electrode may be spatially adjacent to the primary electrode (e.g., within 3 centimeters from the primary electrode). The computing apparatus may be further configured to store a portion of the first signal over a time period (e.g., corresponding to ventricular depolarization, less than or equal to 250 milliseconds, etc.), store a portion of each of the at least one secondary signal over the time period, and compare the portion of the first signal to the portion of each of the at least one secondary signal to provide at least one effectiveness value representative of the effectiveness of the electrode for sensing cardiac signals from the tissue of the patient.

One exemplary method for identifying effective electrodes (e.g., surface electrodes positioned in an array) may include monitoring a first signal from a patient using a primary electrode and monitoring at least one secondary signal from the patient using at least one neighbor electrode. At least one neighbor electrode may be spatially adjacent to the primary electrode (e.g., within 3 centimeters from the primary electrode). The exemplary method may further include storing a portion of the first signal over a time period (e.g., corresponding to ventricular depolarization, less than or equal to 250 milliseconds, etc.), storing a portion of each of the at least one secondary signal over the time period, and comparing the portion of the first signal to the portion of each of the at least one secondary signal to provide at least one effectiveness value (e.g., representing a correlation value between the primary electrode and one neighbor electrode, a Pearson correlation coefficient, etc.) representative of the effectiveness of the electrode for sensing cardiac signals from the tissue of the patient.

An exemplary system for identifying effective electrodes may include electrode means for monitoring a first signal from a patient using a primary electrode and for monitoring at least one secondary signal from the patient using at least one neighbor electrode, where the at least one neighbor electrode is spatially adjacent to the primary electrode, and computing means for storing a portion of the first signal over a time period, for storing a portion of each of the at least one secondary signal over the time period, and for comparing the portion of the first signal to the portion of each of the at least one secondary signal to provide at least one effectiveness value representative of the effectiveness of the electrode for sensing cardiac signals from the tissue of the patient.

An exemplary system for use in cardiac therapy may include electrode apparatus (e.g., a plurality of electrodes configured to be located proximate tissue of a patient) and display apparatus including a graphical user interface (e.g., the graphical user interface may be configured to present information for use in assisting a user in at least one of assessing a patient's cardiac health, evaluating and adjusting cardiac therapy delivered to a patient, and navigating at least one implantable electrode to a region of the patient's heart (e.g., graphically depict at least a portion of anatomy, such as blood vessel anatomy, of the patient's heart for use in assisting a user in navigating at least one implantable electrode to a region of the patient's heart, etc.). The exemplary system may further include computing apparatus coupled to the electrode apparatus and display apparatus. The computing apparatus may be configured to perform an effectiveness test for each electrode of the plurality of electrodes resulting in an effectiveness value for each electrode. To perform the effectiveness test for each electrode, the computing apparatus may be further configured to monitor a first signal from the patient using a primary electrode, monitor at least one secondary signal from the patient using at least one neighbor electrode, where the at least one neighbor electrode is spatially adjacent to the primary electrode, store a portion of the first signal over a time period, and store a portion of each of the at least one secondary signal over the time period. The computing apparatus may be further configured to compare the portion of the first signal to the portion of each of the at least one secondary signal to provide at least one effectiveness value representative of the effectiveness of the electrode for sensing cardiac signals from the tissue of the patient and display, on the graphical user interface, information for use in assisting a user in at least one of assessing a patient's cardiac health, evaluating and adjusting cardiac therapy delivered to a patient, and navigating at least one implantable electrode to a region of the patient's heart (e.g., at least a portion of anatomy, such as blood vessel anatomy, of the patient's heart for use in assisting a user in navigating at least one implantable electrode to a region of the patient's heart, etc.).

An exemplary method for use in cardiac therapy may include monitoring a first signal from a patient using a primary electrode and monitoring at least one secondary signal from the patient using at least one neighbor electrode, where the at least one neighbor electrode is spatially adjacent to the primary electrode. The exemplary method may further include storing a portion of the first signal over a time period, storing a portion of each of the at least one secondary signal over the time period, and comparing the portion of the first signal to the portion of each of the at least one secondary signal to provide at least one effectiveness value representative of the effectiveness of the electrode for sensing cardiac signals from the tissue of the patient. The exemplary method may further include displaying, on a graphical user interface, information for use in assisting a user in at least one of assessing a patient's cardiac health, evaluating and adjusting cardiac therapy delivered to a patient, and navigating at least one implantable electrode to a region of the patient's heart (e.g., at least a portion of anatomy, such as blood vessel anatomy, of the patient's heart for use in assisting a user in navigating at least one implantable electrode to a region of the patient's heart, etc.).

An exemplary system for use in cardiac therapy may include electrode means for monitoring a first signal from a patient using a primary electrode and for monitoring at least one secondary signal from the patient using at least one neighbor electrode, where the at least one neighbor electrode is spatially adjacent to the primary electrode, and computing means for storing a portion of the first signal over a time period, for storing a portion of each of the at least one secondary signal over the time period, and for comparing the portion of the first signal to the portion of each of the at least one secondary signal to provide at least one effectiveness value representative of the effectiveness of the electrode for sensing cardiac signals from the tissue of the patient. The exemplary system may further include display means for displaying, on a graphical user interface, information for use in assisting a user in at least one of assessing a patient's cardiac health, evaluating and adjusting cardiac therapy delivered to a patient, and navigating at least one implantable electrode to a region of the patient's heart (e.g., at least a portion of anatomy, such as blood vessel anatomy, of the patient's heart for use in assisting a user in navigating at least one implantable electrode to a region of the patient's heart, etc.).

In one or more embodiments, the effectiveness value may include a correlation value, and the computing apparatus may be further configured to execute or the method may further include disabling any electrode of the plurality of electrodes having all of their at least one correlation value less than or equal to a selected threshold value (e.g., greater than or equal to 0.7 and less than or equal to about 0.95).

In one or more embodiments, the computing apparatus may be further configured to execute or the method may further include performing an additional effectiveness test for each electrode of the plurality of electrodes resulting in at least one additional correlation value for each electrode if more than a selected percentage of the plurality of electrodes had all of their at least one correlation value less than a selected threshold value.

In one or more embodiments, the computing apparatus may be further configured to execute or the method may further include generating a graphical map including the plurality of electrodes spatially distributed and the effectiveness values of the plurality of electrodes.

One exemplary system for identifying effective electrodes may include electrode apparatus and computing apparatus. The electrode apparatus may include a plurality of electrodes configured to be located proximate tissue of a patient. The computing apparatus may be coupled to the electrode apparatus for sensing electrical activity using the electrode apparatus and may be configured to perform an effectiveness test for each electrode of the plurality of electrodes resulting in an effectiveness value for each electrode. To perform the effectiveness test for each electrode, the computing apparatus may be further configured to monitor a signal from the patient using an electrode, store a portion of the signal over a preset time period, and compare at least one morphological feature of the portion of the signal to at least one physiological indication value to provide the effectiveness value representative of the effectiveness of the electrode for sensing signals from the tissue of the patient. In at least one embodiment, the at least one morphological feature may include at least one of maximum value, minimum value, difference between maximum and minimum value, maximum slope, minimum slope, and difference between maximum slope and minimum slope.

In at least one embodiment, the system or method may be configured to compare morphologic similarity of a signal recorded at an electrode within an electrode array with that of its spatially adjacent neighbor electrodes, e.g., using a Pearson correlation coefficient or a waveform match percentage, etc. The largest value of correlation coefficient or waveform match percentage or the "best match" value of these or similar metrics (e.g., value(s), functions, comparisons, differences, averages, slopes, etc.) may be selected and the process may be repeated for each electrode in the array to find the "best match" value for each electrode. Then, electrodes may be selected to be used (e.g., for further analysis) based on whose "best match" value exceeds a certain threshold (e.g., a correlation coefficient greater than or equal to 0.8 and/or a waveform match percentage score greater than 70). In essence, valid cardiac signals from an electrode within a spatial electrode-array may bear a high degree of similarity with signals from at least one of the neighbor electrodes whereas non-physiological signals (e.g., noise) may be uncorrelated with signals monitored by neighbor electrodes (e.g., valid cardiac signals, noise, etc.).

One exemplary method relates to time correlation of beats sensed from one electrode and includes picking a timing fiducial element (e.g., a V-s or VP marker, a dominant peak or valley on a given ECG lead, etc.) corresponding to each beat, generating a window over a signal of each beat at each electrode about the fiducial, computing a correlation between the windowed signals at each electrode for beats j and j−1, and finding all electrodes which yield a correlation less than or equal to 0.8. In at least one embodiment, the method includes determining if a number of electrodes with a correlation less than or equal to 0.8 exceeds N/2 (where N is the number of electrodes), and if not, eliminating electrodes with correlation less than or equal to 8 and performing analysis with remaining electrodes for beats j and j−1. Further, if the electrodes are within the correlation, then skip beats j and j−1 and move on to the next pair of beats (j, j+1) to repeat analysis and/or adjust electrode positions. The exemplary method may be repeated for each electrode of the N electrodes.

One exemplary method may include comparing morphologic similarity of signals recorded at an electrode within an N array (e.g., 6 or 7 electrodes, 2 or more electrodes, etc.) with that of its spatially adjacent neighbors. The morphologic comparison may employ the Pearson correlation coefficient, waveform match percentage, and/or any number of methods. The method further includes selecting the largest value of correlation coefficient or waveform match percentage or the 'best match' value of these or similar metrics (e.g., value(s), functions, comparisons, differences, averages, slopes, etc.), repeating for each electrode in the array and finding the 'best match' value of that electrode, and selecting signals (e.g., for further analysis) from electrodes in which the 'best match' value exceeds a certain threshold (e.g., a correlation coefficient greater than 0.8 or waveform match percentage score greater than 70).

One exemplary apparatus for automatically selecting electrodes from a surface electrode-array for CRT implant feedback (e.g., evaluating electrical dyssynchrony of the heart of a patient) may include sensing means for sensing a signal from a first one of surface electrode-array in response to the ventricular pacing stimulus, storing means for storing the first sensed signal, sensing means for sensing a second signal from a second one of surface electrode-array in response to the ventricular pacing stimulus, storing means for storing the second sensed signal, processing means for comparing morphologic features between the first and second signals, determining means for determining similarity of the morphological features between the first and second signals, and means for repeatedly processing each electrode of the surface electrode array. Further, the processing means may be configured for determining greatest similarity of the morphological features between two adjacent electrodes of the surface electrode array. The exemplary apparatus may further include selecting means for selecting two adjacent electrodes that exhibit the greatest similarity of the morphological features following the repeated operations for each electrode of the surface electrode array, wherein the selecting means is performed without processing data related to intraventricular synchrony.

The above summary is not intended to describe each embodiment or every implementation of the present disclosure. A more complete understanding will become apparent and appreciated by referring to the following detailed description and claims taken in conjunction with the accompanying drawings.

BRIEF DESCRIPTION OF THE DRAWINGS

FIG. 4 is a diagram of an exemplary system including electrode apparatus, imaging apparatus, display apparatus, and computing apparatus.

DETAILED DESCRIPTION OF EXEMPLARY EMBODIMENTS

Figure 1:
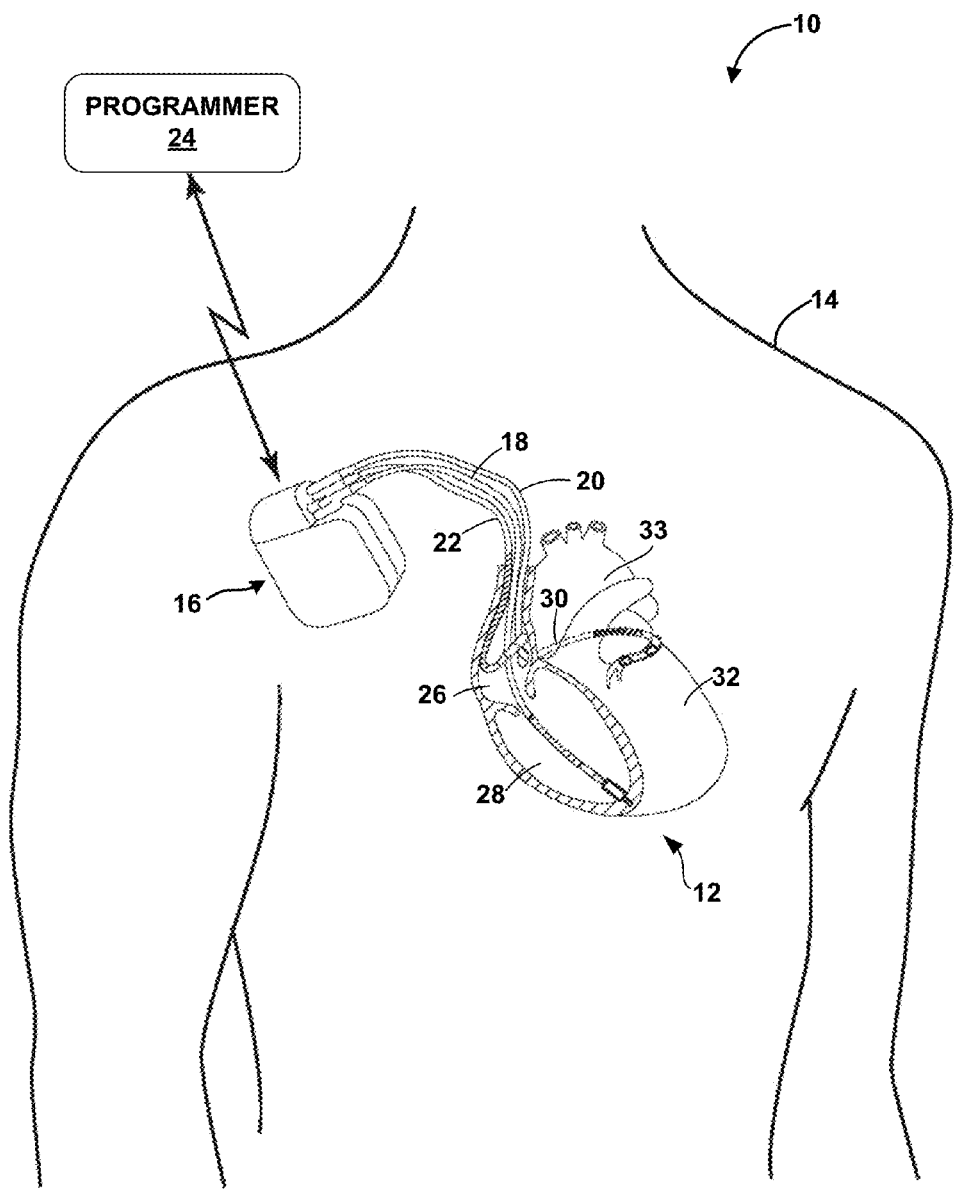
FIG. 1 is a diagram of an exemplary system including an exemplary implantable medical device (IMD).

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary systems, apparatus, and methods shall be described with reference to FIGS. 1-16. It will be apparent to one skilled in the art that elements or processes from one embodiment may be used in combination with elements or processes of the other embodiments, and that the possible embodiments of such methods, apparatus, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

As described herein, various exemplary systems, apparatus, and methods may utilize electrodes configured to sense one or more signals from tissue of a patient and/or deliver therapy to tissue of the patient. For example, electrodes may be included in apparatus such as vests, bands, belts, straps, patches, any wearable garment, t-shirts, bras, hats (e.g., for neural signals), etc. and may be configured to be located externally to the patient in contact with the skin of the patient for, e.g., monitoring cardiac signals (e.g., electrocardiograms) of a patient, mapping a patient's heart, etc. Further, for example, electrodes may be individually located, or placed, on a patient. Further, for example, electrodes may be included in or on apparatus such as a basket catheter, a sock, etc., and may be configured to be located within internal spaces (e.g., cardiac spaces) of a patient, e.g., for cardiac mapping purposes, etc. Further, for example, electrodes may be included as part of an implantable medical device (IMD) and located on one or more leads configured to be located proximate one or more portions of a patient's heart.

In at least one embodiment, a spatial surface electrode array configured to record cardiac signals for computing indices related to electrical dyssynchrony and ventricular activation (which, e.g., may be useful as feedback for cardiac resynchronization therapy implant) may be used. Further, metrics computed from signals from the electrode arrays may be used to, e.g., estimate the time of delivery of left ventricular pacing for optimal fusion for left ventricular-only fusion pacing (e.g., adaptive cardiac resynchronization therapy), estimate scar-burden, etc.

As described herein, various exemplary systems, apparatus, and methods may utilize electrodes configured for any kind of cardiac mapping grid e.g., a sock of electrodes to map electrical activity on the outer surface of the heart, a basket or constellation catheter to map electrical activity within a chamber or the endocardial wall, multipolar leads to map electrical activity of the heart or within a vein in the heart, multi-electrode catheters used for mapping, etc.

Electrodes may be effective or ineffective for sensing signals and/or delivering therapy depending on multiple factors such as whether the electrodes are properly located, whether the electrodes are in sufficient contact with tissue, whether the electrodes or the connections to the electrodes are damaged, etc. As such, a practical problem with a multi-electrode array may be that some of the electrodes may not be effective, and thus, may not provide valid signals (e.g., valid cardiac signals, signals having an adequate signal-to-noise ratio, etc.).

The exemplary systems, apparatus, and methods described herein may provide a way of automated selection of effective electrodes, or electrodes with valid signals, with little error and/or with minimum operator input. The exemplary systems, apparatus, and methods may provide automated selection of effective electrodes based on similarities, or correlations, of a portion, or window, of a signal for an electrode for a cardiac cycle with another portion of the signal for the electrode for another cardiac cycle. Further, the exemplary systems, apparatus, and methods may provide automated selection of effective electrodes based on similarities, or correlations, of a signal of an electrode with a signal of the spatially adjacent neighbor electrode(s). The automated identification of effective electrodes (e.g., capable of sensing valid cardiac signals) and exclusion of electrodes with noise may provide subsequent analysis with signals from the array that is accurate and provides correct assessment of the electrical dyssynchrony of the heart of a patient that may facilitate patient selection for CRT, facilitate placement of implantable leads (e.g., one or more left ventricular leads) and programming of device parameters for CRT during an implantation procedure, reprogramming of device parameters for CRT during a follow-up visit, etc. For example, a user may make a diagnosis, prescribe CRT, position therapy devices, e.g., leads, or adjust or select treatment parameters based on the indicated electrical dyssynchrony.

The exemplary methods and processes described herein may be utilized and implemented by one or more (e.g., two or more, a plurality, etc.) systems, apparatus, and devices that include and/or are coupled to at least one electrode. For example, the exemplary methods and processes may be used by an exemplary therapy system 10 described herein with reference to FIGS. 1-3 and exemplary sensing systems 110, 111 including a spatial electrode-array as described herein with reference to FIGS. 5A-5B. Although only therapy system 10 and sensing systems 110, 111 are described and depicted herein, it is to be understood that the exemplary methods and processes may be used by any system including computing apparatus capable of analyzing signals from one or more electrodes. The computing apparatus, for example, may be located in an external computer or programmer, may be located in an IMD, or may be located on a server attached to a network.

FIG. 1 is a conceptual diagram illustrating an exemplary therapy system 10 that may be used to deliver pacing therapy to a patient 14. Patient 14 may, but not necessarily, be a human. The therapy system 10 may include an implantable medical device 16 (IMD), which may be coupled to leads 18, 20, 22 and/or a programmer 24. The IMD 16 may be, e.g., an implantable pacemaker, cardioverter, and/or defibrillator, that provides electrical signals to the heart 12 of the patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 1, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. The IMD 16 may be configured to determine or identify effective electrodes located on the leads 18, 20, 22 using the exemplary methods and processes described herein. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., AV delay and other various timings, pulse width, amplitude, voltage, burst length, etc. Further, the IMD 16 may be operable to use various electrode configurations to deliver pacing therapy, which may be unipolar, bipolar, quadripoloar, or further multipolar. For example, a multipolar lead may include several electrodes which can be used for delivering pacing therapy. Hence, a multipolar lead system may provide, or offer, multiple electrical vectors to pace from. A pacing vector may include at least one cathode, which may be at least one electrode located on at least one lead, and at least one anode, which may be at least one electrode located on at least one lead (e.g., the same lead, or a different lead) and/or on the casing, or can, of the IMD. While improvement in cardiac function as a result of the pacing therapy may primarily depend on the cathode, the electrical parameters like impedance, pacing threshold voltage, current drain, longevity, etc. may be more dependent on the pacing vector, which includes both the cathode and the anode. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped.

In some examples, a programmer 24, which may be a handheld computing device or a computer workstation, may be used by a user, such as a physician, technician, another clinician, and/or patient, to communicate with the IMD 16 (e.g., to program the IMD 16). For example, the user may interact with the programmer 24 to retrieve information concerning the effectiveness of one or more electrodes, one or more detected or indicated faults associated within the IMD 16 and/or the pacing therapy delivered therewith. The IMD 16 and the programmer 24 may be configured to work together to determine or identify effective electrodes located on the leads 18, 20, 22 using the exemplary methods and processes described herein. For instance, computing apparatus located in one or both of the IMD 16 and the programmer 24 may be configured to analyze or evaluate signals from one or more electrodes to determine the effectiveness of the electrodes. The IMD 16 and the programmer 24 may communicate via wireless communication using any techniques known in the art. Examples of communication techniques may include, e.g., low frequency or radiofrequency (RF) telemetry, but other techniques are also contemplated.

Figure 2A:
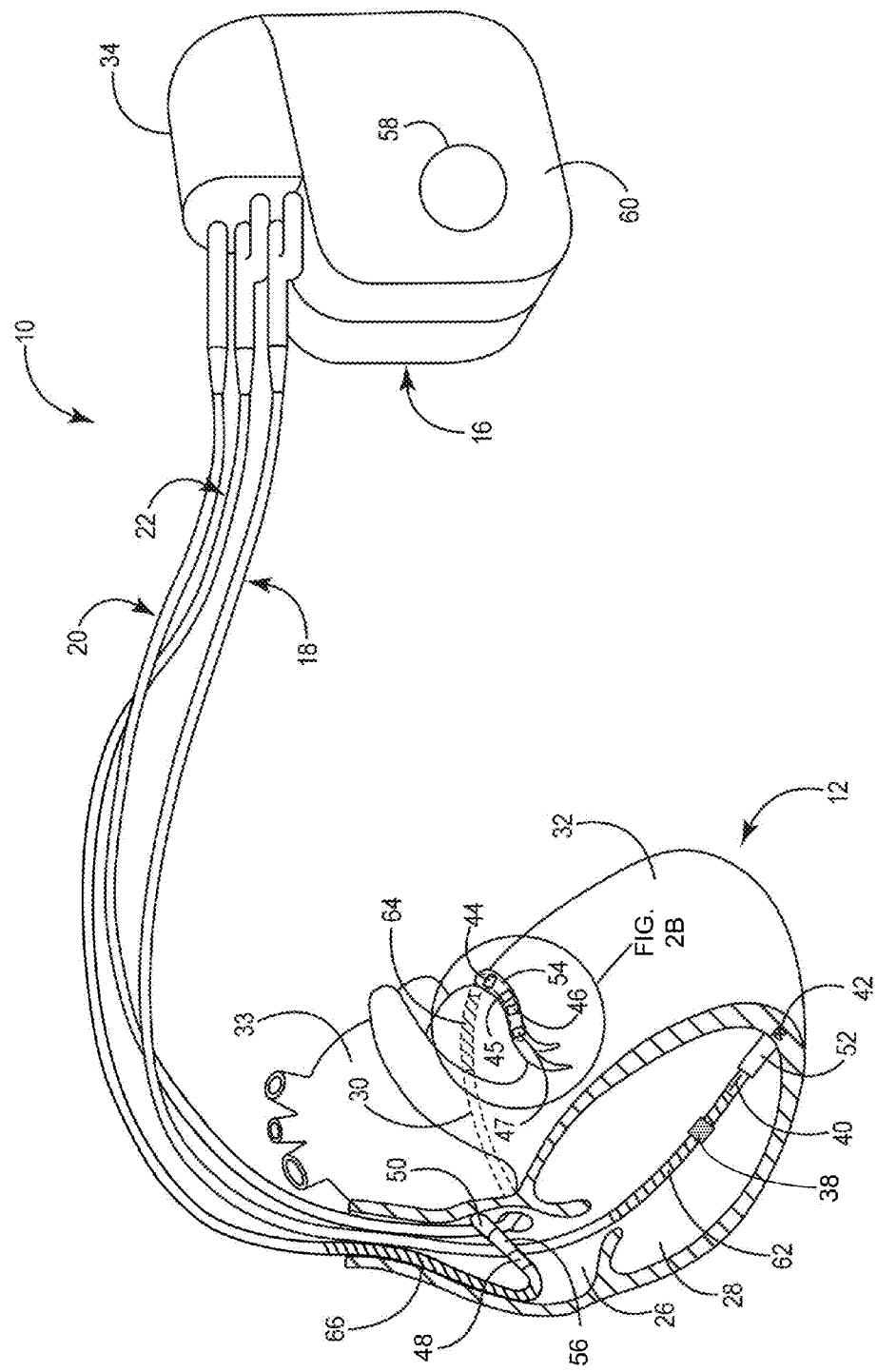
FIG. 2A is a diagram of the exemplary IMD of FIG. 1.
Figure 2B:
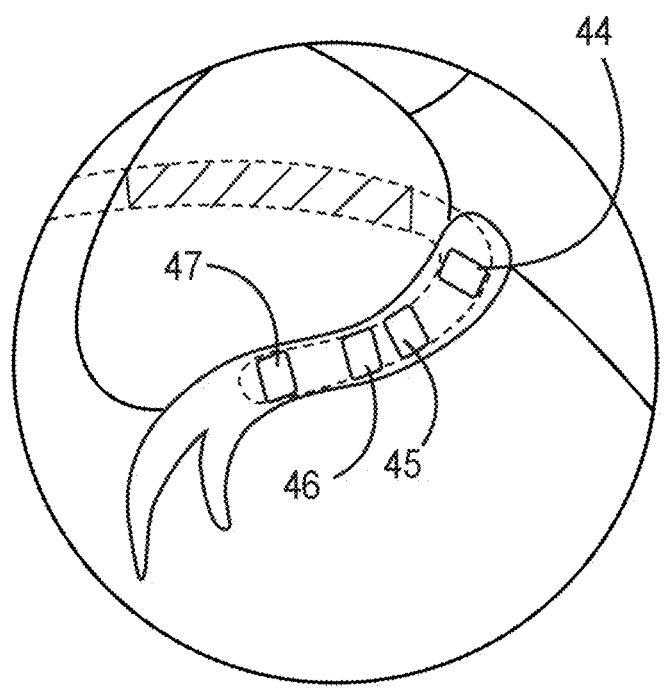
FIG. 2B is a diagram of an enlarged view of a distal end of the electrical lead disposed in the left ventricle of FIG. 2A.

FIG. 2 is a conceptual diagram illustrating the IMD 16 and the leads 18, 20, 22 of therapy system 10 of FIG. 1 in more detail. The leads 18, 20, 22 may be electrically coupled to a therapy delivery module (e.g., for delivery of pacing therapy), a sensing module (e.g., for sensing one or more signals from one or more electrodes configured to contact tissue of a patient), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, the bipolar electrodes 44, 45, 46, 47 are located proximate to a distal end of the lead 20 and the bipolar electrodes 48, 50 are located proximate to a distal end of the lead 22.

The electrodes 40, 44, 45, 46, 47, 48 may take the form of ring electrodes, and the electrodes 42, 50 may take the form of extendable helix tip electrodes mounted retractably within the insulative electrode heads 52, 54, 56, respectively. Each of the electrodes 40, 42, 44, 45, 46, 47, 48, 50 may be electrically coupled to a respective one of the conductors (e.g., coiled and/or straight) within the lead body of its associated lead 18, 20, 22, and thereby coupled to respective ones of the electrical contacts on the proximal end of the leads 18, 20, 22.

Additionally, electrodes 44, 45, 46 and 47 may have an electrode surface area of about 5.3 mm$^2$ to about 5.8 mm$^2$. Electrodes 44, 45, 46, and 47 may also referred to as LV1, LV2, LV3, and LV4, respectively. The LV electrodes (i.e., left ventricle electrode 1 (LV1) 44, left ventricle electrode 2 (LV2) 45, left ventricle electrode 3 (LV3) 46, and left ventricle 4 (LV4) 47 etc.) on the lead 20 can be spaced apart at variable distances. For example, electrode 44 may be a distance of, e.g., about 21 millimeters (mm), away from electrode 45, electrodes 45 and 46 may be spaced a distance of, e.g. about 1.3 mm to about 1.5 mm, away from each other, and electrodes 46 and 47 may be spaced a distance of, e.g. 20 mm to about 21 mm, away from each other.

The electrodes 40, 42, 44, 45, 46, 47, 48, 50 may further be used to sense electrical signals (e.g., morphological waveforms within electrograms (EGM)) attendant to the depolarization and repolarization of the heart 12. The sensed electrical signals may be used to determine whether the electrodes 40, 42, 44, 45, 46, 47, 48, 50 are effective (e.g., capable of sensing valid cardiac signals, capable of delivering therapy, in sufficient contact with cardiac tissue, etc.). The electrical signals are conducted to the IMD 16 via the respective leads 18, 20, 22. In some examples, the IMD 16 may also deliver pacing pulses via the electrodes 40, 42, 44, 45, 46, 47, 48, 50 to cause depolarization of cardiac tissue of the patient's heart 12. In some examples, as illustrated in FIG. 2A, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 45, 46, 47, 48 and 50 may be used for unipolar sensing or pacing in combination with housing electrode 58. In other words, any of electrodes 40, 42, 44, 45, 46, 47, 48, 50, 58 may be used in combination to form a sensing vector, e.g., a sensing vector that may be used to evaluate and/or analyze the effectiveness of pacing therapy. It is generally understood by those skilled in the art that other electrodes can also be selected to define, or be used for, pacing and sensing vectors. Further, any of electrodes 40, 42, 44, 45, 46, 47, 48, 50, 58, which are not being used to deliver pacing therapy, may be used to sense electrical activity during pacing therapy.

As described in further detail with reference to FIGS. 3A-3B, the housing 60 may enclose a therapy delivery module that may include a stimulation generator for generating cardiac pacing pulses and defibrillation or cardioversion shocks, as well as a sensing module for monitoring the patient's heart rhythm. The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity (e.g., for use in determining electrode effectiveness, for use in analyzing pacing therapy effectiveness, etc.) and may be used in combination with any of electrodes 40, 42, 44, 45, 46, 47, 48, 50, 58. In at least one embodiment, the RV elongated electrode 62 may be used to sense electrical activity of a patient's heart during the delivery of pacing therapy (e.g., in combination with the housing electrode 58 forming a RV elongated coil, or defibrillation electrode-to-housing electrode vector).

The configuration of the exemplary therapy system 10 illustrated in FIGS. 1-2 is merely one example. In other examples, the therapy system may include epicardial leads and/or patch electrodes instead of or in addition to the transvenous leads 18, 20, 22 illustrated in FIG. 1. Further, in one or more embodiments, the IMD 16 need not be implanted within the patient 14. For example, the IMD 16 may deliver various cardiac therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

In other examples of therapy systems that provide electrical stimulation therapy to the heart 12, such therapy systems may include any suitable number of leads coupled to the IMD 16, and each of the leads may extend to any location within or proximate to the heart 12. For example, other examples of therapy systems may include three transvenous leads located as illustrated in FIGS. 1-2. Still further, other therapy systems may include a single lead that extends from the IMD 16 into the right atrium 26 or the right ventricle 28, or two leads that extend into a respective one of the right atrium 26 and the right ventricle 28.

Figure 3A:
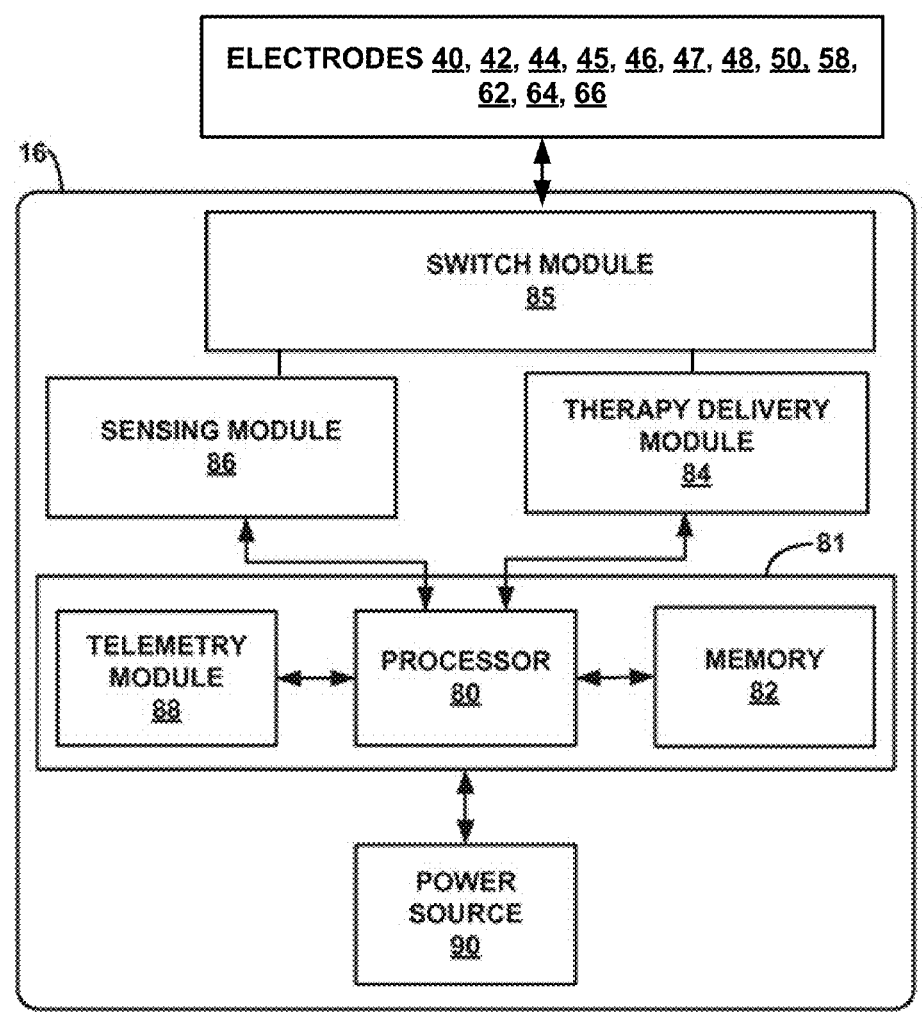
FIG. 3A is a block diagram of an exemplary IMD, e.g., the IMD of FIGS. 1-2.

FIG. 3A is a functional block diagram of one exemplary configuration of the IMD 16. As shown, the IMD 16 may include a control module 81, a therapy delivery module 84 (e.g., which may include a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random access memory (RAM), read-only memory (ROM), non-volatile RAM (NVRAM), electrically-erasable programmable ROM (EEPROM), flash memory, and/or any other digital media. An exemplary capture management module may be the left ventricular capture management (LVCM) module described in U.S. Pat. No. 7,684,863 issued Mar. 23, 2010, which is incorporated herein by reference in its entirety.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may be used to determine the effectiveness of the electrodes 40, 42, 44, 45, 46, 47, 48, 50, 58, 62, 64, 66 using the exemplary methods and/or processes described herein according to a selected one or more programs, which may be stored in the memory 82. Further, the control module 81 may control the therapy delivery module 84 to deliver therapy (e.g., electrical stimulation therapy such as pacing) to the heart 12 according to a selected one or more therapy programs, which may be stored in the memory 82. More specifically, the control module 81 (e.g., the processor 80) may control various parameters of the electrical stimulus delivered by the therapy delivery module 84 such as, e.g., AV delays, pacing pulses with the amplitudes, pulse widths, frequency, or electrode polarities, etc., which may be specified by one or more selected therapy programs (e.g., AV delay adjustment programs, pacing therapy programs, pacing recovery programs, capture management programs, etc.). As shown, the therapy delivery module 84 is electrically coupled to electrodes 40, 42, 44, 45, 46, 47, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 45, 46, 47, 48, 50, 58, 62, 64, 66.

For example, therapy delivery module 84 may deliver pacing stimulus (e.g., pacing pulses) via ring electrodes 40, 44, 45, 46, 47, 48 coupled to leads 18, 20, and 22, respectively, and/or helical tip electrodes 42, 50 of leads 18, 20, and 22. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured deliver one or more of these types of stimulation in the form of other signals, such as sine waves, square waves, and/or other substantially continuous time signals.

The IMD 16 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 45, 46, 47, 48, 50, 58, 62, 64, 66 (e.g., a pair of electrodes for delivery of therapy to a pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 45, 46, 47, 48, 50, 58, 62, 64, 66 to monitor electrical activity of the heart 12, e.g., electrocardiogram (ECG)/electrogram (EGM) signals, etc. The ECG/EGM signals may be used to identify the effectiveness of each of the electrodes 40, 42, 44, 46, 48, 50, 58, 62, 64, 66 (e.g., by monitoring or measuring the signals for analysis by the control module 81, the programmer 24, etc.). Further, the ECG/EGM signals may be used to measure or monitor activation times (e.g., ventricular activations times, etc.), heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may be also be used with the sensing module 86 to select which of the available electrodes are used, or enabled, to, e.g., sense electrical activity of the patient's heart (e.g., one or more electrical vectors of the patient's heart using any combination of the electrodes 40, 42, 44, 45, 46, 47, 48, 50, 58, 62, 64, 66). Likewise, the switch module 85 may be also be used with the sensing module 86 to select which of the available electrodes are not to be used (e.g., disabled) to, e.g., sense electrical activity of the patient's heart (e.g., one or more electrical vectors of the patient's heart using any combination of the electrodes 40, 42, 44, 45, 46, 47, 48, 50, 58, 62, 64, 66). In some examples, the control module 81 may select the electrodes that function as sensing electrodes via the switch module within the sensing module 86, e.g., by providing signals via a data/address bus.

In some examples, sensing module 86 includes a channel that includes an amplifier with a relatively wider pass band than the R-wave or P-wave amplifiers. Signals from the selected sensing electrodes may be provided to a multiplexer, and thereafter converted to multi-bit digital signals by an analog-to-digital converter for storage in memory 82, e.g., as an electrogram (EGM). In some examples, the storage of such EGMs in memory 82 may be under the control of a direct memory access circuit. The control module 81 (e.g., using the processor 80) may employ digital signal analysis techniques to characterize the digitized signals stored in memory 82 to analyze and/or classify one or more morphological waveforms of the EGM signals to determine which electrodes are effective (e.g., operable for capturing valid signals), determine which electrodes are ineffective (e.g., inoperable for capturing valid signals), determine pacing therapy effectiveness, etc. For example, the processor 80 may be configured to determine, or obtain, one more features of one or more sensed morphological waveforms within one or more electrical vectors of the patient's heart and store the one or more features within the memory 82 for use in comparing features, values, etc. of the waveforms to determine effectiveness of the electrodes.

In some examples, the control module 81 may operate as an interrupt driven device, and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding one or more series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as the programmer 24 as described herein with respect to FIG. 1. For example, under the control of the processor 80, the telemetry module 88 may receive downlink telemetry from and send uplink telemetry to the programmer 24 with the aid of an antenna, which may be internal and/or external. The processor 80 may provide the data to be uplinked to the programmer 24 and the control signals for the telemetry circuit within the telemetry module 88, e.g., via an address/data bus. In some examples, the telemetry module 88 may provide received data to the processor 80 via a multiplexer.

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

Figure 3B:
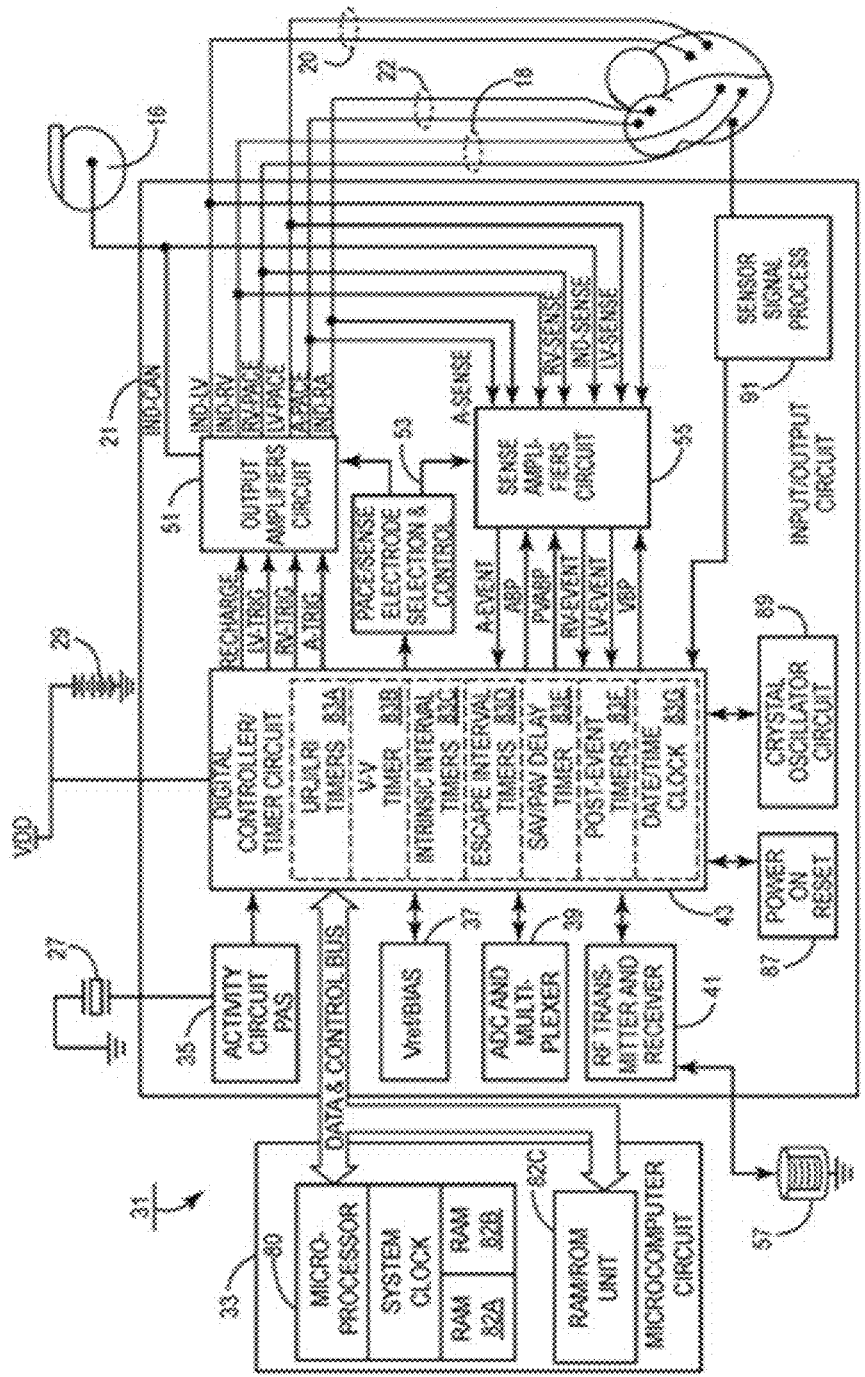
FIG. 3B is another block diagram of an exemplary IMD (e.g., an implantable pulse generator) circuitry and associated leads employed in the system of FIGS. 1-2 for providing three sensing channels and corresponding pacing channels.

FIG. 3B is another embodiment of a functional block diagram for IMD 16. FIG. 3B depicts bipolar RA lead 22, bipolar RV lead 18, and bipolar LV CS lead 20 without the LA CS pace/sense electrodes and coupled with an implantable pulse generator (IPG) circuit 31 having programmable modes and parameters of a bi-ventricular DDD/R type known in the pacing art. In turn, the sensor signal processing circuit 91 indirectly couples to the timing circuit 83 and via data and control bus to microcomputer circuitry 33. The IPG circuit 31 is illustrated in a functional block diagram divided generally into a microcomputer circuit 33 and a pacing circuit 21. The pacing circuit 21 includes the digital controller/timer circuit 83, the output amplifiers circuit 51, the sense amplifiers circuit 55, the RF telemetry transceiver 41, the activity sensor circuit 35 as well as a number of other circuits and components described below.

Crystal oscillator circuit 89 provides the basic timing clock for the pacing circuit 21, while battery 29 provides power. Power-on-reset circuit 87 responds to initial connection of the circuit to the battery for defining an initial operating condition and similarly, resets the operative state of the device in response to detection of a low battery condition. Reference mode circuit 37 generates stable voltage reference and currents for the analog circuits within the pacing circuit 21, while analog to digital converter ADC and multiplexer circuit 39 digitizes analog signals and voltage to provide real time telemetry if a cardiac signals from sense amplifiers 55, for uplink transmission via RF transmitter and receiver circuit 41. Voltage reference and bias circuit 37, ADC and multiplexer 39, power-on-reset circuit 87 and crystal oscillator circuit 89 may correspond to any of those presently used in current marketed implantable cardiac pacemakers.

If the IPG is programmed to a rate responsive mode, the signals output by one or more physiologic sensor are employed as a rate control parameter (RCP) to derive a physiologic escape interval. For example, the escape interval is adjusted proportionally to the patient's activity level developed in the patient activity sensor (PAS) circuit 35 in the depicted, exemplary IPG circuit 31. The patient activity sensor 27 is coupled to the IPG housing and may take the form of a piezoelectric crystal transducer as is well known in the art and its output signal is processed and used as the RCP. Sensor 27 generates electrical signals in response to sensed physical activity that are processed by activity circuit 35 and provided to digital controller/timer circuit 83. Activity circuit 35 and associated sensor 27 may correspond to the circuitry disclosed in U.S. Pat. No. 5,052,388 issued Oct. 1, 1991 and U.S. Pat. No. 4,428,378 issued Jan. 31, 1984, each of which is incorporated herein by reference in its entirety. Similarly, the exemplary systems, apparatus, and methods described herein may be practiced in conjunction with alternate types of sensors such as oxygenation sensors, pressure sensors, pH sensors and respiration sensors, all well known for use in providing rate responsive pacing capabilities. Alternately, QT time may be used as the rate indicating parameter, in which case no extra sensor is required. Similarly, the exemplary embodiments described herein may also be practiced in non-rate responsive pacemakers.

Data transmission to and from the external programmer is accomplished by way of the telemetry antenna 57 and an associated RF transceiver 41, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and marker channel pulses indicating the occurrence of sensed and paced depolarizations in the atrium and ventricle, as are well known in the pacing art.

Microcomputer 33 contains a microprocessor 80 and associated system clock and on-processor RAM and ROM chips 82A and 82B, respectively. In addition, microcomputer circuit 33 includes a separate RAM/ROM chip 82C to provide additional memory capacity. Microprocessor 80 normally operates in a reduced power consumption mode and is interrupt driven. Microprocessor 80 is awakened in response to defined interrupt events, which may include A-TRIG, RV-TRIG, LV-TRIG signals generated by timers in digital timer/controller circuit 83 and A-EVENT, RV-EVENT, and LV-EVENT signals generated by sense amplifiers circuit 55, among others. The specific values of the intervals and delays timed out by digital controller/timer circuit 83 are controlled by the microcomputer circuit 33 by way of data and control bus from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 80 may also serve to define variable, operative AV delay intervals and the energy delivered to each ventricle.

In one embodiment, microprocessor 80 is a custom microprocessor adapted to fetch and execute instructions stored in RAM/ROM unit 82 in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 80.

Digital controller/timer circuit 83 operates under the general control of the microcomputer 33 to control timing and other functions within the pacing circuit 320 and includes a set of timing and associated logic circuits of which certain ones pertinent to the present invention are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals or the V-V conduction interval, escape interval timers 83D for timing A-A, V-A, and/or V-V pacing escape intervals, an AV delay interval timer 83E for timing the A-LVp delay (or A-RVp delay) from a preceding A-EVENT or A-TRIG, a post-ventricular timer 83F for timing post-ventricular time periods, and a date/time clock 83G.

The AV delay interval timer 83E is loaded with an appropriate delay interval for one ventricular chamber (e.g., either an A-RVp delay or an A-LVp delay as determined using known methods) to time-out starting from a preceding A-PACE or A-EVENT. The interval timer 83E triggers pacing stimulus delivery, and can be based on one or more prior cardiac cycles (or from a data set empirically derived for a given patient).

The post-event timer 83F time out the post-ventricular time period following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 33. The post-ventricular time periods include the PVARP, a post-atrial ventricular blanking period (PAVBP), a ventricular blanking period (VBP), a post-ventricular atrial blanking period (PVARP) and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any AV delay, and an atrial blanking period (ABP) during which atrial sensing is disabled. It should be noted that the starting of the post-atrial time periods and the AV delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 80 also optionally calculates AV delays, post-ventricular time periods, and post-atrial time periods that vary with the sensor based escape interval established in response to the RCP(s) and/or with the intrinsic atrial rate.

The output amplifiers circuit 51 contains a RA pace pulse generator (and a LA pace pulse generator if LA pacing is provided), a RV pace pulse generator, and a LV pace pulse generator or corresponding to any of those presently employed in commercially marketed cardiac pacemakers providing atrial and ventricular pacing. In order to trigger generation of an RV-PACE or LV-PACE pulse, digital controller/timer circuit 83 generates the RV-TRIG signal at the time-out of the A-RVp delay (in the case of RV pre-excitation) or the LV-TRIG at the time-out of the A-LVp delay (in the case of LV pre-excitation) provided by AV delay interval timer 83E (or the V-V delay timer 83B). Similarly, digital controller/timer circuit 83 generates an RA-TRIG signal that triggers output of an RA-PACE pulse (or an LA-TRIG signal that triggers output of an LA-PACE pulse, if provided) at the end of the V-A escape interval timed by escape interval timers 83D.

The output amplifiers circuit 51 includes switching circuits for coupling selected pace electrode pairs from among the lead conductors and the IND_CAN electrode 20 to the RA pace pulse generator (and LA pace pulse generator if provided), RV pace pulse generator and LV pace pulse generator. Pace/sense electrode pair selection and control circuit 53 selects lead conductors and associated pace electrode pairs to be coupled with the atrial and ventricular output amplifiers within output amplifiers circuit 51 for accomplishing RA, LA, RV and LV pacing.

The sense amplifiers circuit 55 contains sense amplifiers corresponding to any of those presently employed in contemporary cardiac pacemakers for atrial and ventricular pacing and sensing. High impedance P-wave and R-wave sense amplifiers may be used to amplify a voltage difference signal that is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 83 controls sensitivity settings of the atrial and ventricular sense amplifiers 55.

The sense amplifiers are typically uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND-CAN electrode 20 from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND-CAN electrode 20 to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 83. Similarly, left atrial depolarizations or P-waves in the LA-SENSE signal that are sensed by the LA sense amplifier, if provided, result in a LA-EVENT signal that is communicated to the digital controller/timer circuit 83. Ventricular depolarizations or R-waves in the RV-SENSE signal are sensed by a ventricular sense amplifier result in an RV-EVENT signal that is communicated to the digital controller/timer circuit 83. Similarly, ventricular depolarizations or R-waves in the LV-SENSE signal are sensed by a ventricular sense amplifier result in an LV-EVENT signal that is communicated to the digital controller/timer circuit 83. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

As described herein, various exemplary systems, methods, and interfaces may be configured to use electrode apparatus including external electrodes, imaging apparatus, display apparatus, and computing apparatus to noninvasively assist a user (e.g., a physician) in selecting one or more locations (e.g., implantation site regions) proximate a patient's heart for one or more implantable electrodes and/or to navigate one or more implantable electrodes to the selected location(s). An exemplary system 100 including electrode apparatus 110, imaging apparatus 120, display apparatus 130, and computing apparatus 140 is depicted in FIG. 4.

The electrode apparatus 110 as shown includes a plurality of electrodes incorporated, or included within a band wrapped around the chest, or torso, of a patient 14. The electrode apparatus 110 is operatively coupled to the computing apparatus 140 (e.g., through one or more wired electrical connections, wirelessly, etc.) to provide electrical signals from each of the electrodes to the computing apparatus 140 for analysis. Exemplary electrode apparatus may be described in U.S. Provisional Patent Application 61/913,759 entitled "Bioelectric Sensor Device and Methods" and filed on Dec. 9, 2013 and U.S. patent application Ser. No. 14/227,719 entitled "Bioelectric Sensor Device and Methods" and filed on Mar. 27, 2014 and issued as U.S. Pat. No. 9,320,446 on Apr. 26, 2016, each of which is incorporated herein by reference in its entirety. Further, exemplary electrode apparatus 110 will be described in more detail in reference to FIGS. 5A-5B.

The imaging apparatus 120 may be any type of imaging apparatus configured to image, or provide images of, at least a portion of the patient in a non-invasive manner. For example, the imaging apparatus 120 may not use any components or parts that may be located within the patient to provide images of at least a portion of the patient except non-invasive tools such as contrast solution. It is to be understood that the exemplary systems, methods, and interfaces described herein may noninvasively assist a user (e.g., a physician) in selecting a location proximate a patient's heart for an implantable electrode, and after the exemplary systems, methods, and interfaces have provided noninvasive assistance, the exemplary systems, methods, and interfaces may then provide assistance to implant, or navigate, an implantable electrode into the patient, e.g., proximate the patient's heart.

For example, after the exemplary systems, methods, and interfaces have provided noninvasive assistance, the exemplary systems, methods, and interfaces may then provide image guided navigation that may be used to navigate leads including electrodes, leadless electrodes, wireless electrodes, catheters, etc., within the patient's body. Further, although the exemplary systems, methods, and interfaces are described herein with reference to a patient's heart, it is to be understood that the exemplary systems, methods, and interfaces may be applicable to any other portion of the patient's body.

The imaging apparatus 120 may be configured to capture, or take, x-ray images (e.g., two dimensional x-ray images, three dimensional x-ray images, etc.) of the patient 14. The imaging apparatus 120 may be operatively coupled (e.g., through one or more wired electrical connections, wirelessly, etc.) to the computing apparatus 140 such that the images captured by the imaging apparatus 120 may be transmitted to the computing apparatus 140. Further, the computing apparatus 140 may be configured to control the imaging apparatus 120 to, e.g., configure the imaging apparatus 120 to capture images, change one or more settings of the imaging apparatus 120, etc.

It will be recognized that while the imaging apparatus 120 as shown in FIG. 4 may be configured to capture x-ray images, any other alternative imaging modality may also be used by the exemplary systems, methods, and interfaces described herein. For example, the imaging apparatus 120 may be configured to capture images, or image data, using isocentric fluoroscopy, bi-plane fluoroscopy, ultrasound, computed tomography (CT), multi-slice computed tomography (MSCT), magnetic resonance imaging (MRI), high frequency ultrasound (HIFU), optical coherence tomography (OCT), intra-vascular ultrasound (IVUS), two dimensional (2D) ultrasound, three dimensional (3D) ultrasound, four dimensional (4D) ultrasound, intraoperative CT, intraoperative MRI, etc. Further, it is to be understood that the imaging apparatus 120 may be configured to capture a plurality of consecutive images (e.g., continuously) to provide video frame data. In other words, a plurality of images taken over time using the imaging apparatus 120 may provide motion picture data. Additionally, the images may also be obtained and displayed in two, three, or four dimensions. In more advanced forms, four-dimensional surface rendering of the heart or other regions of the body may also be achieved by incorporating heart data or other soft tissue data from an atlas map or from pre-operative image data captured by MRI, CT, or echocardiography modalities. Image datasets from hybrid modalities, such as positron emission tomography (PET) combined with CT, or single photon emission computer tomography (SPECT) combined with CT, could also provide functional image data superimposed onto anatomical data to be used to confidently reach target locations within the heart or other areas of interest.

The display apparatus 130 and the computing apparatus 140 may be configured to display and analyze data such as, e.g., surrogate electrical activation data, image data, mechanical motion data, etc. gathered, or collected, using the electrode apparatus 110 and the imaging apparatus 120 to noninvasively assist a user in location selection of an implantable electrode. In at least one embodiment, the computing apparatus 140 may be a server, a personal computer, or a tablet computer. The computing apparatus 140 may be configured to receive input from input apparatus 142 and transmit output to the display apparatus 130. Further, the computing apparatus 140 may include data storage that may allow for access to processing programs or routines and/or one or more other types of data, e.g., for driving a graphical user interface configured to noninvasively assist a user in location selection of an implantable electrode, etc.

The computing apparatus 140 may be operatively coupled to the input apparatus 142 and the display apparatus 130 to, e.g., transmit data to and from each of the input apparatus 142 and the display apparatus 130. For example, the computing apparatus 140 may be electrically coupled to each of the input apparatus 142 and the display apparatus 130 using, e.g., analog electrical connections, digital electrical connections, wireless connections, bus-based connections, network-based connections, internet-based connections, etc. As described further herein, a user may provide input to the input apparatus 142 to manipulate, or modify, one or more graphical depictions displayed on the display apparatus 130 to view and/or select one or more target or candidate locations of a portion of a patient's heart as further described herein.

Although as depicted the input apparatus 142 is a keyboard, it is to be understood that the input apparatus 142 may include any apparatus capable of providing input to the computing apparatus 140 to perform the functionality, methods, and/or logic described herein. For example, the input apparatus 142 may include a mouse, a trackball, a touchscreen (e.g., capacitive touchscreen, a resistive touchscreen, a multi-touch touchscreen, etc.), etc. Likewise, the display apparatus 130 may include any apparatus capable of displaying information to a user, such as a graphical user interface 132 including graphical depictions of anatomy of a patient's heart, images of a patient's heart, graphical depictions of locations of one or more electrodes, graphical depictions of one or more target or candidate locations, alphanumeric representations of one or more values, graphical depictions or actual images of implanted electrodes and/or leads, etc. For example, the display apparatus 130 may include a liquid crystal display, an organic light-emitting diode screen, a touchscreen, a cathode ray tube display, etc.

The graphical user interfaces 132 displayed by the display apparatus 130 may include, or display, one or more regions used to display graphical depictions, to display images, to allow selection of one or more regions or areas of such graphical depictions and images, etc. As used herein, a "region" of a graphical user interface 132 may be defined as a portion of the graphical user interface 132 within which information may be displayed or functionality may be performed. Regions may exist within other regions, which may be displayed separately or simultaneously. For example, smaller regions may be located within larger regions, regions may be located side-by-side, etc. Additionally, as used herein, an "area" of a graphical user interface 132 may be defined as a portion of the graphical user interface 132 located with a region that is smaller than the region it is located within. Exemplary systems and interfaces may be described in U.S. Provisional Patent Application 61/913,743 entitled "Noninvasive Cardiac Therapy Evaluation" and filed on Dec. 9, 2013 and U.S. patent application Ser. No. 14/228,009 entitled "Noninvasive Cardiac Therapy Evaluation" and filed on Mar. 27, 2014, each of which is incorporated herein by reference in its entirety.

The processing programs or routines stored and/or executed by the computing apparatus 140 may include programs or routines for computational mathematics, matrix mathematics, decomposition algorithms, compression algorithms (e.g., data compression algorithms), calibration algorithms, image construction algorithms, signal processing algorithms (e.g., Fourier transforms, fast Fourier transforms, etc.), standardization algorithms, comparison algorithms, vector mathematics, or any other processing required to implement one or more exemplary methods and/or processes described herein. Data stored and/or used by the computing apparatus 140 may include, for example, image data from the imaging apparatus 120, electrical signal data from the electrode apparatus 110, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein, or any other data that may be necessary for carrying out the one and/or more processes or methods described herein.

In one or more embodiments, the exemplary systems, methods, and interfaces may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The one or more programs used to implement the systems, methods, and/or interfaces described herein may be provided using any programmable language, e.g., a high level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the exemplary systems, methods, and/or interfaces may be implemented using a computer readable storage medium, configured with a computer program, where the storage medium so configured causes the computer to operate in a specific and predefined manner to perform functions described herein. Further, in at least one embodiment, the exemplary systems, methods, and/or interfaces may be described as being implemented by logic (e.g., object code) encoded in one or more non-transitory media that includes code for execution and, when executed by a processor, is operable to perform operations such as the methods, processes, and/or functionality described herein.

The computing apparatus 140 may be, for example, any fixed or mobile computer system (e.g., a controller, a microcontroller, a personal computer, mini computer, tablet computer, etc.). The exact configuration of the computing apparatus 130 is not limiting, and essentially any device capable of providing suitable computing capabilities and control capabilities (e.g., graphics processing, etc.) may be used. As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by computing apparatus 140 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

Figure 5A:
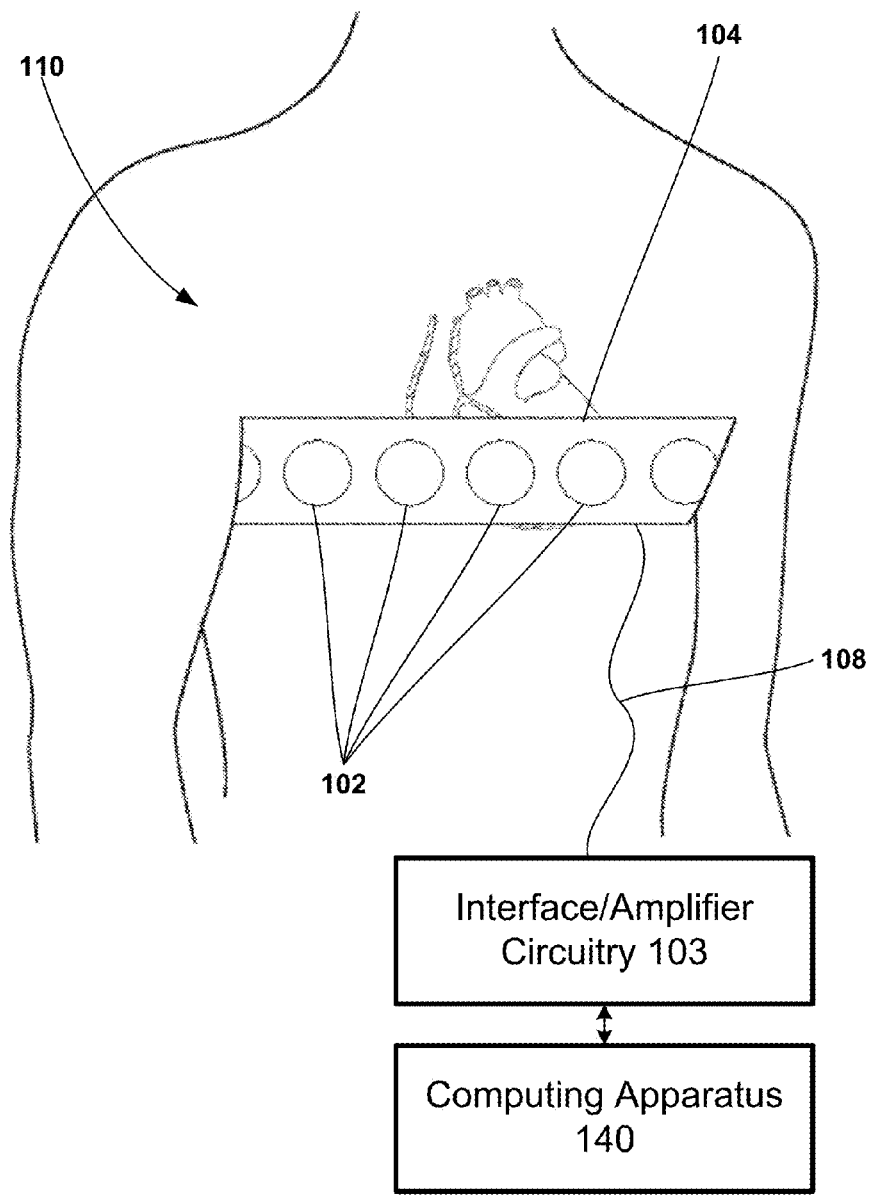
FIGS. 5A-5B are conceptual diagrams illustrating exemplary systems for measuring torso-surface potentials.
Figure 5B:
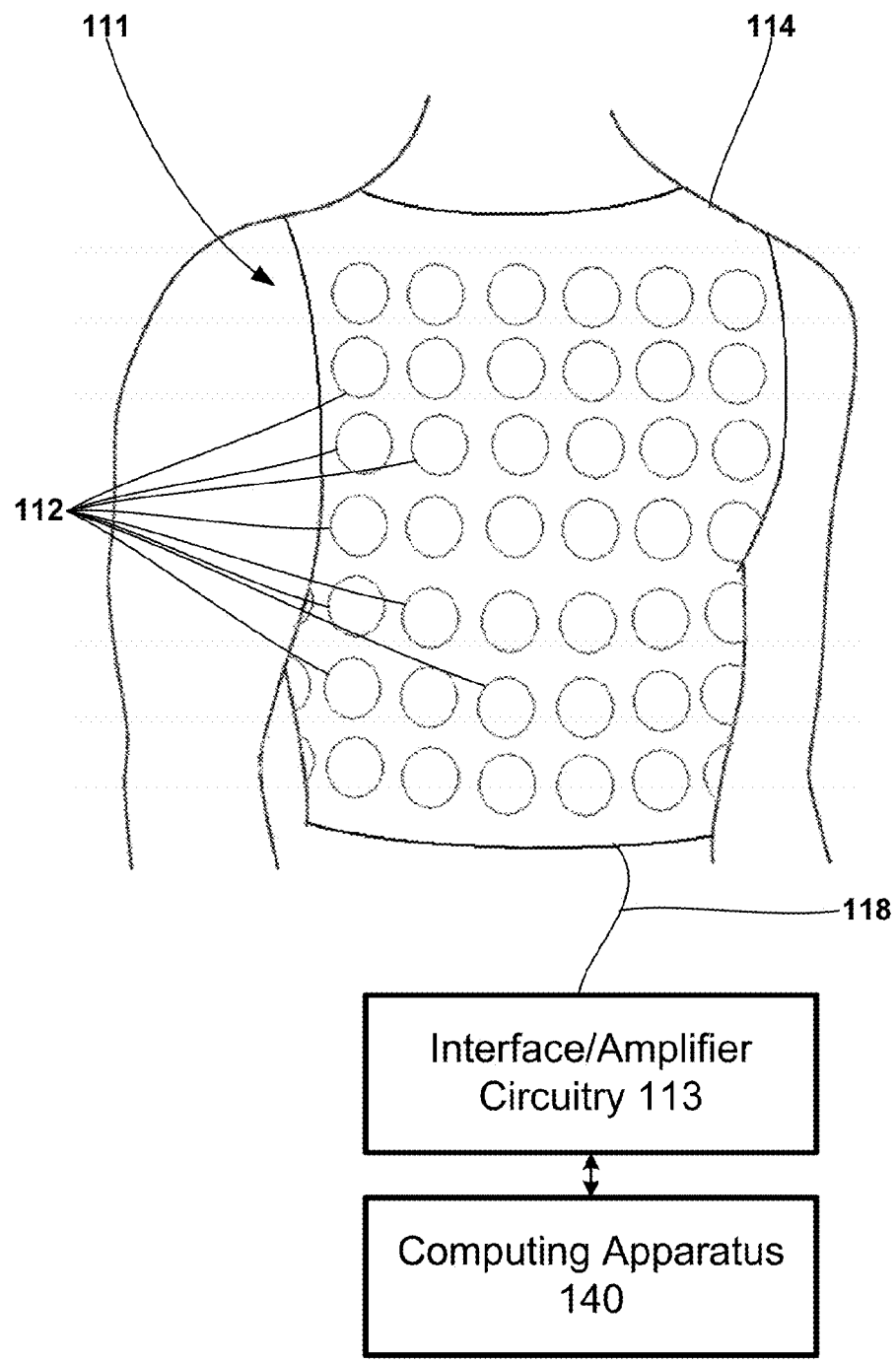

FIGS. 5A-5B are conceptual diagrams illustrating exemplary electrode systems and apparatus for measuring body-surface potentials and, more particularly, torso-surface potentials. As shown in FIG. 5A, the exemplary electrode system 110 includes a set or array of electrodes 102, a strap 104, interface/amplifier circuitry 103, and computing apparatus 140 such as described herein with reference to FIG. 4. The electrodes 102 are attached, or coupled, to the strap 104 that is configured to be wrapped around the torso of patient such that the electrodes 102 surround the patient's heart. As further illustrated, the electrodes 102 may be positioned around the circumference of patient, including the posterior, lateral, and anterior surfaces of the torso of patient. In other examples, electrodes 102 may be positioned on any one or more of the posterior, lateral, and anterior surfaces of the torso. Further, the electrodes 102 may be electrically connected to interface/amplifier circuitry 103 via wired connection 108. The interface/amplifier circuitry 103 may be configured to amplify the signals from the electrodes 102 and provide the signals to the computing apparatus 140. Other exemplary systems may use a wireless connection to transmit the signals sensed by electrodes 102 to the interface/amplifier circuitry 103 and, in turn, the computing apparatus 140, e.g., as channels of data.

Although in the example of FIG. 5A, the system 110 includes a strap 104, in other examples any of a variety of mechanisms, e.g., tape or adhesives, may be employed to aid in the spacing and placement of electrodes 102. In other examples, the electrodes 102 may be placed individually on the torso of a patient. Further, in other examples, electrodes 102 (e.g., arranged in an array) may be part of, or located within, patches, vests, and/or other means of securing the electrodes 102 to the torso of the patient.

The electrodes 102 may be configured to surround the heart of the patient and record, or monitor, the electrical signals associated with the depolarization repolarization of the heart after the signals have propagated through the torso of patient. Each of the electrodes 102 may be used in a unipolar configuration to sense the torso-surface potentials that reflect the cardiac signals. The interface/amplifier circuitry 103 may also be coupled to a return or indifferent electrode (not shown) which may be used in combination with each of electrodes 102 for unipolar sensing. In some examples, there may be about 12 to about 50 electrodes 102 spatially distributed around the torso of patient. Other configurations may have more or fewer electrodes 102.

The computing apparatus 140 may record and analyze the torso-surface potential signals sensed by electrodes 102 and amplified/conditioned by the interface/amplifier circuitry 103. For example, the sensing and computing apparatus described in U.S. Pat. App. Pub. No. 2012/0283587 A1 published Nov. 8, 2012 and U.S. Pat. App. Pub. No. 2012/0284003 A1 published Nov. 8, 2012, each of which is incorporated herein by reference in its entirety, may be used to record and analyze torso-surface potential signals. The computing apparatus 140 may be configured to analyze the signals from the electrodes 102 to determine whether each electrode of the electrodes 102 is effective (e.g., operable for monitoring or sensing signals from the tissue, or skin, of the patient).

FIG. 5B illustrates another exemplary electrode system 111 that includes a plurality of electrodes 112 configured to surround the heart of the patient and record, or monitor, the electrical signals associated with the depolarization and repolarization of the heart after the signals have propagated through the torso of patient. The electrode system 111 may include a vest 114 upon which the plurality of electrodes is attached, or to which they are coupled. In at least one embodiment, the plurality, or array, of electrodes 112 may be used to evaluate electrical dyssynchrony in the heart of the patient. Similar to the system 110, the system 111 may include interface/amplifier circuitry 113 electrically coupled to each of the electrodes 112 through a wired connection 118 and configured to transmit signals from the electrodes 112 to a computing apparatus 140. As illustrated, the electrodes 112 may be distributed over the torso of patient, including, for example, the anterior, lateral, and posterior surfaces of the torso of patient.

The vest 114 may be formed of fabric, or any other material, with the electrodes 112 attached to thereto. The vest 114 may be configured to maintain the position and spacing of electrodes 112 on the torso of the patient. Further, the vest 114 may be marked to assist in determining the location of the electrodes 112 on the surface of the torso of the patient. The vest 114 may also be one piece or in multiple pieces to allow simple placement on the anterior and posterior of the patient using anatomical landmarks such as the spine and sternum of the patient. Further, the vest 114 may also be, or be used in conjunction with, a belt or patch(es) including electrodes 112. In some examples, there may be about 25 to about 256 electrodes 112 distributed around the torso of the patient, though other configurations may have more or fewer electrodes 112.

The exemplary systems, apparatus, and/or methods described herein are configured to identify effective electrodes, and the systems including electrodes, computing apparatus, and display apparatus described herein with reference to FIGS. 1-5 may utilize the exemplary systems, apparatus, and/or methods. More specifically, the exemplary systems, apparatus, and/or methods may be used to determine which electrodes in the systems of FIGS. 1-5 may be effective (or ineffective) for sensing signals from tissue of the patient and/or pacing tissue of the patient. After it is determined which electrodes are effective, the electrodes may be used to assist a user (e.g., a physician) in determining effective pacing vectors, navigating or locating one or more electrodes (e.g., implantable electrodes, electrodes on leads, leadless/wireless electrodes, etc.) to one or more regions of a patient's heart for therapy, to monitor and display information with respect to the cardiac health of the patient (e.g., before, during, and after implantation of cardiac therapy device), etc.

When the band 104 of the surface electrode array system 110 of FIG. 5A or the vest 114 of the surface electrode array system 111 of FIG. 5B is located, or placed, on a patient, some of the electrodes 102, 112 may not be in sufficient contact (e.g., not proper contact, not full or complete contact, partial contact, etc.) with the skin of the patient, and thus, may not provide a valid signal (e.g., cardiac signal) from the patient. As such, the exemplary systems, apparatus, and/or methods may be used with the systems 110, 111 of FIGS. 5A-5B to determine which electrodes 102, 112 are effective for sensing valid electrical activity (e.g., not noise) from the skin of the patient.

Further, for example, when the leads 18, 20, 22 of the system 10 of FIGS. 1-3 are located, or implanted, in a patient's heart, some of the electrodes 40, 42, 44, 45, 46, 47, 48, 50, 58, 62, 64, 66 may not be in sufficient contact (e.g., not proper contact, not full or complete contact, partial contact, etc.) with the cardiac tissue of the patient, which may not provide sufficient sensing of cardiac signals and/or pacing functionality. As such, the exemplary systems, apparatus, and/or methods may be used with the system 10 of FIGS. 1-3 to determine which electrodes 40, 42, 44, 45, 46, 47, 48, 50, 58, 62, 64, 66 are effective for sensing valid electrical activity (e.g., not noise) from the cardiac tissue of the patient and/or delivering effective electrical therapy to the cardiac tissue of the patient.

Figure 6:
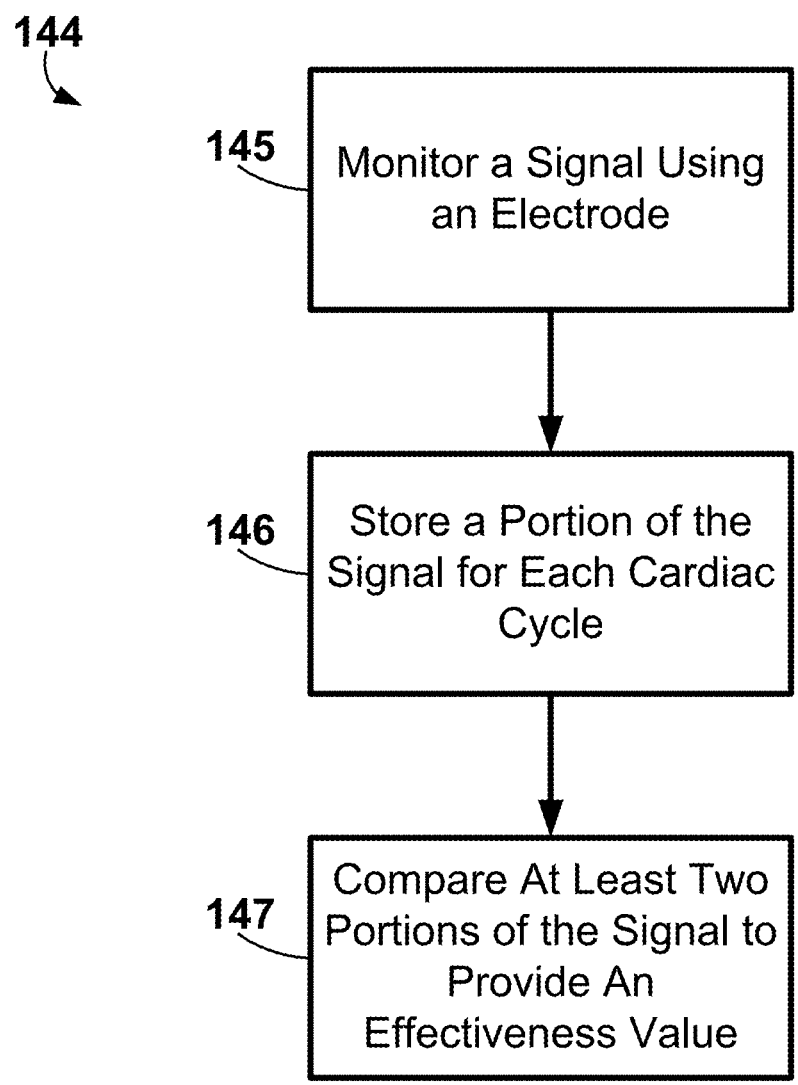
FIG. 6 is a block diagram of an exemplary method of identifying an effective electrode using single signal correlation.

An exemplary method 144 for identifying effective electrodes in a plurality of electrodes is depicted in FIG. 6. The exemplary method 144 may be described as using single signal analysis because, for each electrode, only the signal from that electrode is used to determine whether the electrode is effective. Although the exemplary method 144 is described herein with respect to determining the effectiveness of a single electrode, it is to be understood that the method 144 could be repeated (e.g., performed sequentially one electrode at a time) or performed simultaneously for a plurality of electrodes such that each electrode of a plurality of electrodes may be evaluated and determined to be either effective or ineffective.

Before executing method 144, an electrode may be located proximate tissue of a patient configured to sense a signal from the patient. For example, an electrode 102 of the system 110 may be located proximate the torso of a patient and configured to monitor a signal from the skin of the torso of the patient. To determine whether the electrode is effective, the exemplary method 144 may monitor a signal from the electrode 145.

The exemplary method 144 may then store a portion of the signal from the electrode for each cardiac cycle of at least two cardiac cycles 146. For example, a portion from a first cardiac cycle may be stored and a portion from a second cardiac cycle (e.g., subsequent the first cardiac cycle) may be stored. A portion of the signal may be described as being a "window" or "snapshot" of the signal taken over a preset time period. For example, the preset time period of the portion of the signal may be between about 80 milliseconds (ms) to about 400 ms, such as, e.g., about 80 ms, about 100 ms, about 150 ms, about 200 ms, about 250 ms, about 300 ms, about 350 ms, about 400 ms, etc. The time period may be described as being "preset" because, e.g., the time period may be set by a user.

Each portion of the signal may correspond to the same time frame within each cardiac cycle. In other words, each portion may occur during the same part or region of the cardiac cycle. To identify or select the portion of the signal that corresponds to the same time frame within each cardiac cycle, the exemplary method 144 may use one or more recurring fiducial elements, markers, or values within the signal or any other cardiac parameter. In other words, to store a portion of the signal for each cardiac cycle 146, the exemplary method 144 may store a portion of the signal based on a recurring fiducial element within a cardiac signal or parameter.

The recurring fiducial element may include one or more of a ventricular event (e.g., a ventricular pace, a ventricular sense, etc.), an atrial event (e.g., an atrial pace, an atrial sense, etc.), a maximum value (e.g., a peak of a QRS complex, a peak of a P-wave, etc.), a minimum value, a maximum slope value (e.g., a maximum slope of an R-wave, etc.), an amplitude or slope of atrial or ventricular depolarization signal, a crossing of a predefined threshold, etc. The timing of recurring fiducial element, or time when the recurring fiducial occurs, may be used to base the portion of the signal upon. For example, the start of fiducial element may start the time frame or window to store a portion of the signal.

For example, the exemplary method 144 may store a 250 ms portion of the signal starting from a ventricular pace (i.e., the selected fiducial element). As such, a first portion may be recorded, or stored, from the start of a ventricular pace for 250 ms during a first a cardiac cycle, and a second portion may be recorded, or stored, from the start of a ventricular pace for 250 ms during a second cardiac cycle that is subsequent to the first cardiac cycle.

After at least two portions have been stored 146, the exemplary method 144 may compare the at least two stored portions of the signal to provide an effectiveness value 147 or other effectiveness information representative of such comparison. The effectiveness value may be representative of the effectiveness of the electrode for using in sensing signals from the tissue of the patient and/or delivering electrical therapy to the tissue of the patient.

The effectiveness value may be a correlation value or coefficient (e.g., a Pearson correlation coefficient). Although not shown, the exemplary method 144 may then enable (e.g., use) the electrode if is determined to be effective and/or may disable (e.g., not use or utilize) the electrode if is determined to be ineffective. To determine whether an electrode is effective based on an effectiveness value, the effectiveness value may be compared to a threshold value. If the electrode has an effectiveness value greater than or equal to the threshold value, then the electrode may be enabled. If the electrode has an effectiveness value below the threshold value, then the electrode may be disabled.

In an embodiment where the effectiveness value is a Pearson correlation coefficient, the threshold value may be between about 0.5 and 0.98 such as, e.g., 0.8. For example, the threshold value may be greater than or equal to about 0.5, greater than or equal to about 0.6, greater than or equal to about 0.7, greater than or equal to about 0.75, greater than or equal to about 0.8, etc. and/or may be less than or equal to about 0.8, less than or equal to about 0.85, less than or equal to about 0.9, less than or equal to about 0.95, less than or equal to about 0.98, etc.

In an embodiment where the effectiveness value is a waveform match percentage, the threshold value may be between about 50% and 100% such as, e.g., 70%. Waveform match percentages may be generated and/or calculated using various techniques and/or process, e.g., as described in U.S. Pat. No. 6,393,316 B1 entitled "METHOD AND APPARATUS FOR DETECTION AND TREATMENT OF CARDIAC ARRHYTHMIAS" issued May 21, 2002, which is incorporated herein by reference in its entirety. For example, the threshold value may be greater than or equal to about 50%, greater than or equal to about 60%, greater than or equal to about 70%, greater than or equal to about 75%, greater than or equal to about 80%, etc. and/or may be less than or equal to about 100%, less than or equal to about 95%, less than or equal to about 90%, less than or equal to about 85%, less than or equal to about 88%, etc.

Prior to the comparison, the portions of the cardiac signal may be aligned to compensate for noise-related jitter of the fiducial element with each portion. For example, the portions may be aligned based on timing of at least one of the following features of the signal, or fiducial element: maximum slope, minimum slope, maximum value, minimum value within each window etc. In at least one embodiment, alignment may be performed based on timing of the maximum value, the minimum value, and/or the greater of the magnitudes of the maximum value and the minimum value.

In at least one embodiment, an exemplary graphical user interface may graphically depict a plurality of electrodes correlating to a plurality of actual, physical electrodes in a contact with the patient. The graphical user interface may identify which electrodes are determined to be effective and which electrodes are determined to be ineffective. A user may use the graphical user interface to enable or disable each of the electrodes. In other words, a user may be allowed to turn "off" or turn "on" each electrode via a user interface/program that controls the amplifiers and A/D converters.

Further, a vest or belt of electrodes may not fit correctly (e.g., too large, too small, etc.) about a patient such that one or more of the electrodes may not make contact with the patient so as to provide an effective electrical signal. A user (e.g., a physician) may recognize which electrodes may not be effective and use a graphical user interface to disable the electrodes recognized to be ineffective.

Figure 7:
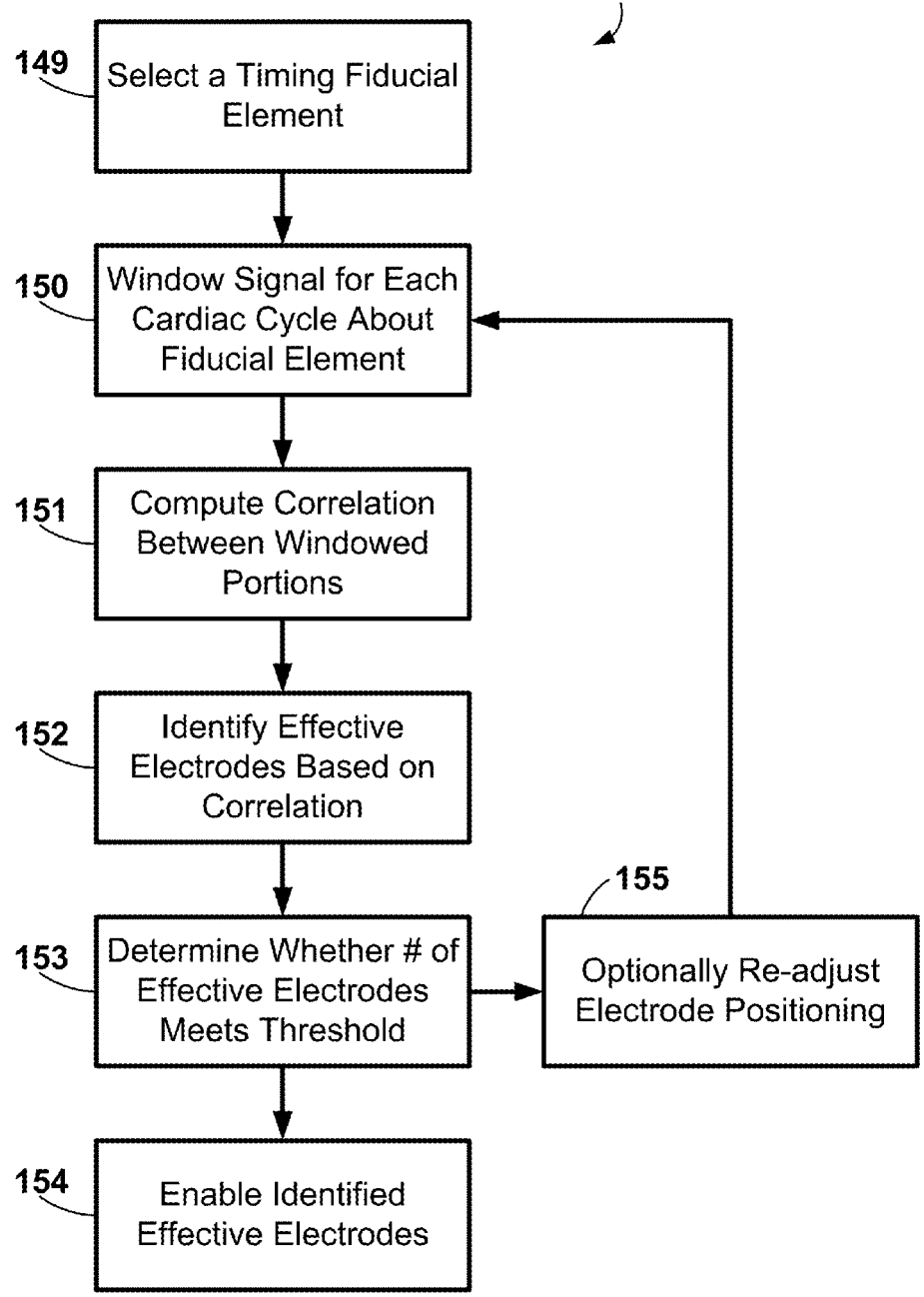
FIG. 7 is a block diagram of an exemplary method of identifying one or more effective electrodes using single signal correlation.

Another exemplary method 156 for identifying effective electrodes of a plurality of electrodes is depicted in FIG. 7. The method 156 may include selecting a recurring timing fiducial element 149 to base the windowing (e.g., framing, cropping, etc.) portions of the signal for each cardiac cycle. As described herein, the recurring timing fiducial element may be one or more morphological features of a cardiac signal such as, e.g., a maximum value of the signal, etc. The method 156 may then window a portion of the signal of at least two heart beats, or cardiac cycles 150. For example, if the fiducial element is a maximum value and the preset time period is 200 ms, the exemplary method 156 may window 200 ms portions of the signal about the maximum value for each cardiac cycle 150. The window may be selected such that the recurring time fiducial element is centered within the window (time frame), starts the window, ends the window, etc. In other words, the recurring timing fiducial element may start the capture window, stop the capture window, or be located halfway through the capture window.

After at least two windowed signals have been stored or captured 150, a correlation may be computed between the two windowed portions 151 resulting in an effectiveness value. As described herein, in at least one embodiment, a Pearson correlation coefficient may be calculated as the effectiveness value, or in another embodiment, a waveform match percentage may be calculated as the effectiveness value. Based on the effectiveness value, the method 156 may identify if the electrode is effective 152, e.g., using a threshold value, etc.

The method 156 may determine the effectiveness of more than one electrode simultaneously since the signal of each electrode is compared to itself and is not determined based on other signals. In other words, the method 156 may be described as being configured to identify an effective electrode using single signal correlation. For example, if an exemplary system includes eight electrodes, the signal of each of the eight electrodes may be windowed about a fiducial element for at least two cardiac cycles 150 and a correlation may be computed between the at least two windowed signals 151 for each electrode resulting in an effectiveness value for each electrode. The effectiveness value may be used to identify which of the 8 electrodes are effective.

Exemplary systems may require a selected number or percentage of effective electrodes, e.g., of those electrodes available in the array. For example, the method 156 may further include a check to confirm that a selected number of electrodes are effective 153. If such a selected number of electrodes out of the provided electrodes are determined to be effective 153, then the method 156 may proceed to enabling the effective electrodes 154 and indicating that the system has been initialized, is ready for sensing procedures, etc. To determine if enough electrodes out of the provided electrodes are effective, the method 156 may compare the number of effective electrodes to a threshold value. For example, in a system that includes 50 electrodes, the threshold may be 40 electrodes. Thus, if the 40 or more electrodes are determined to be effective, then the method 156 may proceed to enabling the 40 effective electrodes and disabling the 10 ineffective electrodes.

If it is determined that not enough electrodes are effective 153, the method 156 may optionally re-adjust the electrode positioning 155. For example, a system or device may suggest to a user to re-adjust the electrode positioning. In the case of a vest including a plurality of electrodes, a user may adjust the vest such that more electrodes make better contact with the skin of the user. Further, the method 156 may restart the identification procedure for each of the electrodes if it is determined that not enough electrodes are effective 153 (as signified by the return arrow to windowing the signal of each beat about a fiducial element 150).

Signals, such as, e.g., cardiac signals, collected, or monitored from an electrode in a spatial sensor-array may be correlative (e.g., highly correlative) with signals monitored by neighbor electrodes in the spatial sensor-array (e.g., electrodes located in relatively close proximity to one another) if the signals are physiological. Likewise, a lack of, or low, correlation between signals monitored may indicate "bad" or non-physiologic signals. In other words, low correlation may indicate the one or more electrodes are ineffective (e.g., ineffective for sensing, ineffective for delivering therapy, etc.). One or more exemplary automated methods, or algorithms, are described herein that may use correlation coefficients between signals collected by multiple electrodes to determine "bad" or ineffective electrodes (or to determine "good" or effective electrodes).

Figure 8:
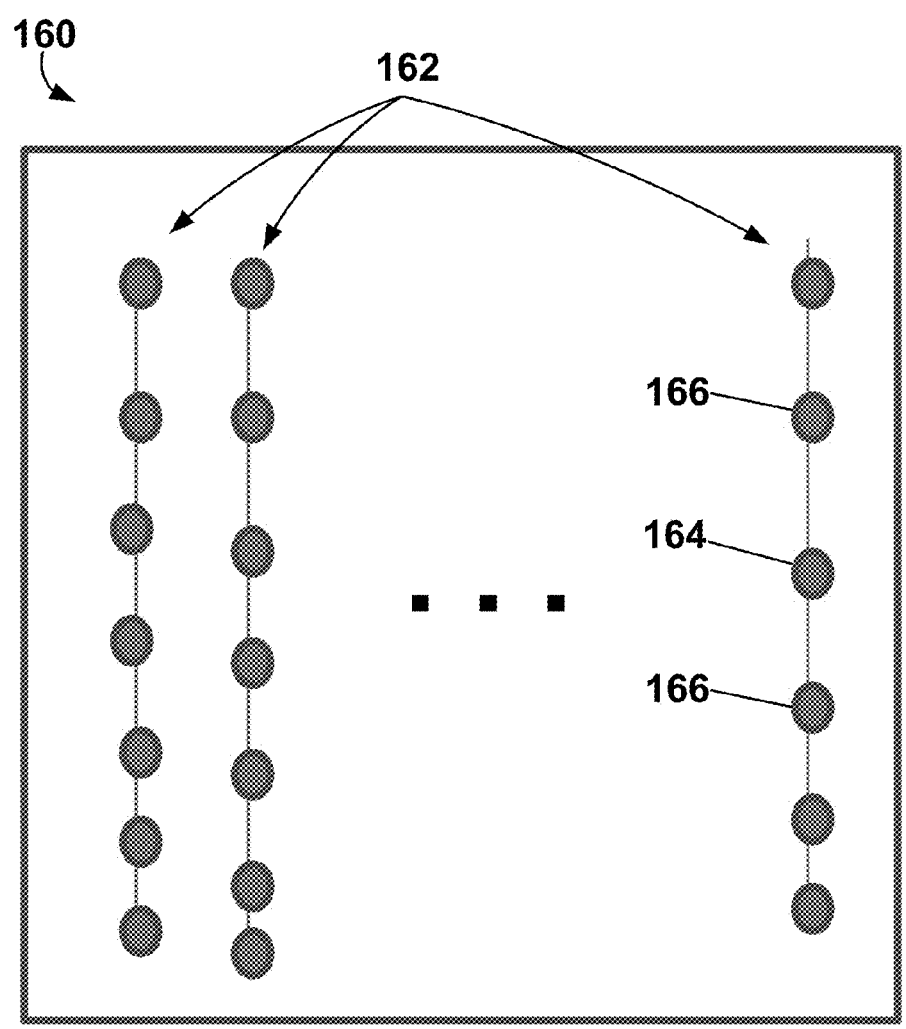
FIG. 8 is a diagram of an exemplary electrode array.

For example, an exemplary array of electrodes 160 is depicted in FIG. 8. In at least one embodiment, the array of electrodes 160 may be configured to be located adjacent the torso of a patient. As shown, the array 160 includes a plurality of rows 162 of electrodes. Each row 162 may be described as being spaced apart from another. In other words, each row 162 is spatially oriented which respect to each other. Further, each electrode within each row 162 is spaced apart from one another. In at least one embodiment, the spacing between rows and/or electrodes within each row may be uniform. In at least one embodiment, the space between electrodes may be about 0.5 centimeters (cm) to about 5 cm, such as, e.g., 1 cm, 2 cm, 3 cm, etc. In at least one embodiment, the space between electrodes may be as small as 1 millimeter (mm) (e.g., for intracardiac mapping). In at least one embodiment, the space between electrodes may be about 0.1 mm to about 5 mm, such as, e.g., 0.2 mm, 0.5 mm, 1 mm, 1.5 mm, 2.0 mm, 3.0 mm, etc.

Further, for purposes of description of the exemplary methods and/or processes, the electrodes may be described in terms of primary electrodes and proximate neighbor electrodes. The primary electrode is the electrode that is being evaluated for effectiveness using the exemplary methods and/or processes while the proximate neighbor electrodes are the one or more electrodes that may be used to evaluate the effectiveness of the primary electrode.

As shown in the array 160, primary electrode 164 has two proximate neighbor electrodes 166. Although in this example, the primary electrode 164 has two proximate neighbor electrodes 166, in other embodiments, the primary electrode may have only one proximate neighbor electrode or more than two proximate neighbor electrodes. Although the neighbor electrodes 166 are located in the same row as the primary electrode 164 as depicted, in other embodiments, neighbor electrodes 166 may be located in rows adjacent to the row containing the primary electrode 164.

In at least one embodiment, the correlation of a depolarization signal at each electrode may be evaluated with two adjacent neighbor electrodes (e.g., vertical neighbors or electrodes along the same line). For example, a correlation may be computed, or generated, between the depolarization signal monitored by a primary electrode and the depolarization signal monitored at each of two adjacent neighbor electrodes resulting in two correlation values (e.g., each correlation value corresponding to a pair of electrodes that includes the primary electrode). The greater of the two correlation values may be assigned to the primary electrode and used to determine whether the primary electrode is effective or ineffective. The method or algorithm may be represented as follows: Greater (corrcoef(signal(j), signal(j+1)), corrcoef (signal(j), signal(j−1)). Primary electrodes located at an extremity, or end, of a vertical line of electrodes will only have one vertical neighbor electrode, and thus, a single correlation value may be generated, or computed, for that primary electrode.

Figure 9:
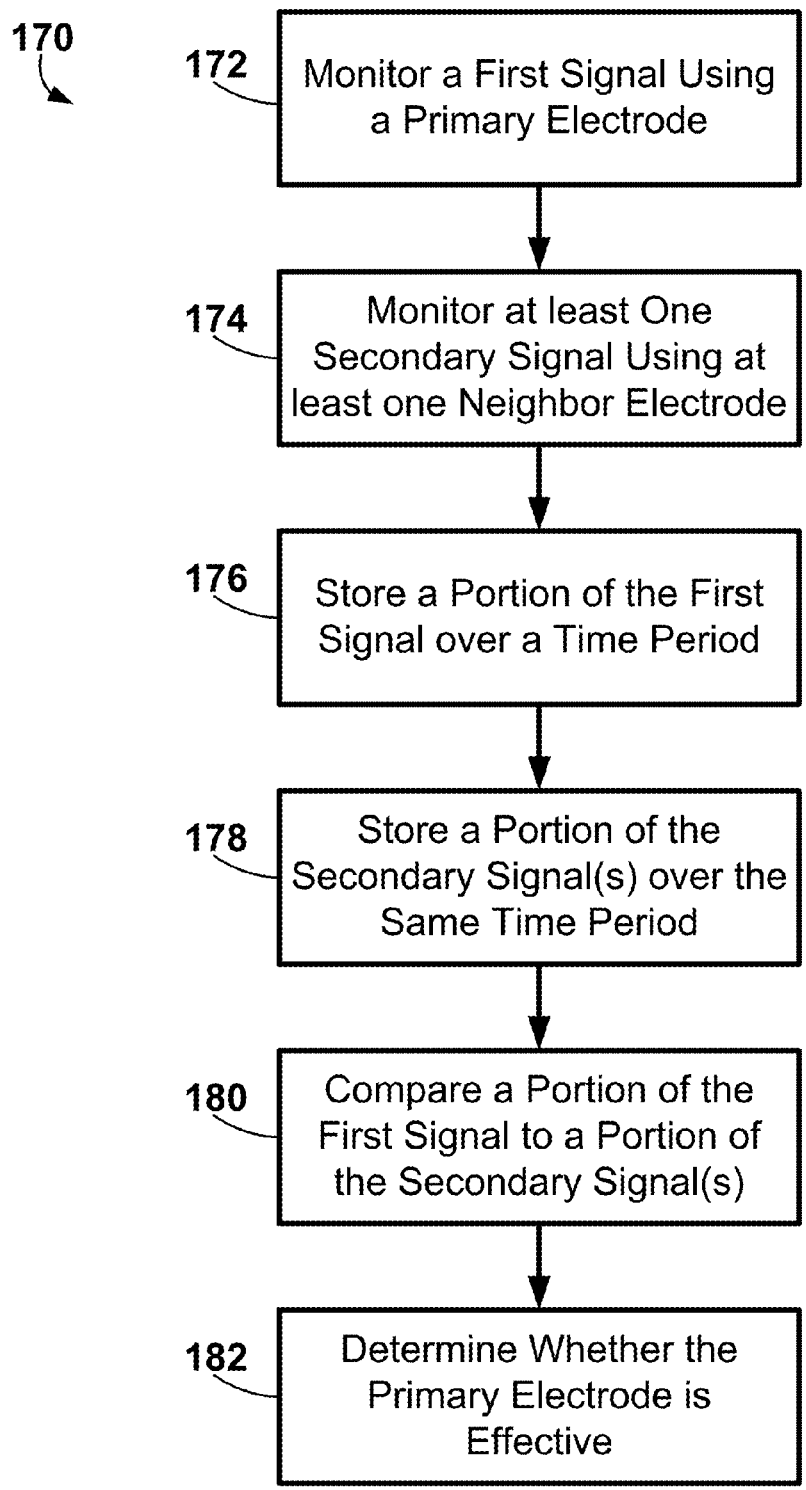
FIG. 9 is a block diagram of an exemplary method of identifying an effective electrode using spatial signal correlation, e.g. using the electrode array of FIG. 8.

An exemplary method of identifying an effective electrode using spatial signal correlation, e.g., using the electrode array of FIG. 8, is depicted in FIG. 9. The method 170 includes monitoring a first signal from a patient using a primary electrode 172 and monitoring one or more secondary signals from the patient using one or more neighbor electrodes 174. The neighbor electrode may be located spatially adjacent the primary electrode (e.g., within 3 cm of the primary electrode). For example, each neighbor electrode may be located within a pre-selected, or certain, proximity to the primary electrode.

A portion of the first signal may be stored to be used in the comparative analysis 176 and a portion of each of the one or more secondary signals 178 may be stored to also be used in the comparative analysis. To provide useful data, the portions of the first signal and the one or more secondary signals may be chosen to include data other than an ambient signal (e.g., flat line signal, etc.) and/or noise. For example, the portions of the first signal and the one or more secondary signals may correspond to a fiducial element (e.g., a particular event) within a cardiac waveform (e.g., per cardiac cycle) such as, e.g., ventricular depolarization, atrial depolarization, ventricular repolarization, atrial repolarization, etc.

Further, each of the portions of the first signal and the secondary signals may be window or cropped for a selected, or preset, period of time such as, e.g., 250 milliseconds. The period of time may be about 100 milliseconds (ms) to about 400 ms, such as, e.g., about 100 ms, about 150 ms, about 200 ms, about 250 ms, about 300 ms, about 400 ms, etc. Further, each portion of the first signal and the secondary signals may occur (and thus, be recorded) at the same time. For example, the portion of the first signal may be recorded at the exact same time the portion of the secondary signals is recorded. In other words, the portions of the first signal and the secondary signals may be stored over the same time period.

To determine the effectiveness of the primary electrode, the portion of the first signal may be compared to the portion of each of the secondary signals to provide an effectiveness value for each comparison 180. For example, if two adjacent neighbor electrodes providing two secondary signals are utilized, a first comparison may occur between the portion of the first signal and the portion of the first secondary signal to provide a first effectiveness value, and a second comparison may occur between the portion of the first signal and the portion of the second secondary signal to provide a second effectiveness value. Each of effectiveness values for each primary electrode may represent a correlation value between the primary electrode and the neighbor electrode. Similar to the methods 130, 140 described herein with reference to FIGS. 5-6, the effectiveness values may be correlation coefficients (e.g., Pearson correlation coefficients), waveform match percentages, etc.

The exemplary method 170 may then determine whether the primary electrode is effective by comparing the effectiveness values to a threshold value 182 similar to the threshold values described herein with respect to the methods 130, 140 of FIGS. 5-6. In this embodiment, each primary electrode may have multiple effectiveness values since the signal of the primary electrode may be compared to a secondary signal from more than one secondary electrode. If multiple effectiveness values are generated, various statistical processes may be used to provide a single value. For example, the greatest effectiveness value may be used. Further, for example, an average of the effectiveness values may be used. Still further, effectiveness values that are outliers may be excluded while the remaining effectiveness values may be used.

In at least one embodiment, if one of the effectiveness values is greater than a threshold value, then the method 170 may determine that the primary electrode is effective 182. In other words, a single strong correlation between the primary electrode and an adjacent neighbor electrode may indicate that the primary electrode is effective.

Conversely, in at least one embodiment, if all of the effectiveness values are less than a threshold value, then the method 170 may determine that the primary electrode is ineffective 182. In other words, no strong correlation between the primary electrode and an adjacent neighbor electrode may indicate that the primary electrode is ineffective.

The method 170 may be repeated for each electrode of an electrode array or IMD until each electrode is determined to be effective or ineffective. Further, the method 170 may be performed sequentially with one electrode at a time or in parallel by recording the signal from each electrode of a plurality of electrodes at the same time.

Although not shown, the exemplary systems and apparatus described herein may provide a display to depict, or show, information with respect to the effectiveness of the electrodes. For example, a graphical representation of an array of electrodes may be depicted on the display and information with respect to the effectiveness of each of the electrodes may be depicted proximate each of the electrodes. In at least one embodiment, a graphical map may be generated that includes a plurality of electrodes spatially distributed and an effectiveness values for each of the plurality of electrodes depicted proximate the electrodes. A user may use the graphical map to determine areas of the array that may not be located, or fitted, properly to the user to create sufficient contact between the electrodes and the tissue of the patient.

Further, similar to the method 156 of FIG. 7, an additional effectiveness test for each electrode may be performed or repeated if more than a selected percentage of the plurality of electrodes were identified as being ineffective. For example, if 50% of the electrodes had all of their at least one correlation value less than a selected threshold value, then the method 170 may repeat or retest the array of electrodes. Prior to retesting, a user may re-adjust the array of electrodes to, e.g., provide better contact between the electrodes and the tissue of the patient.

Figure 10:
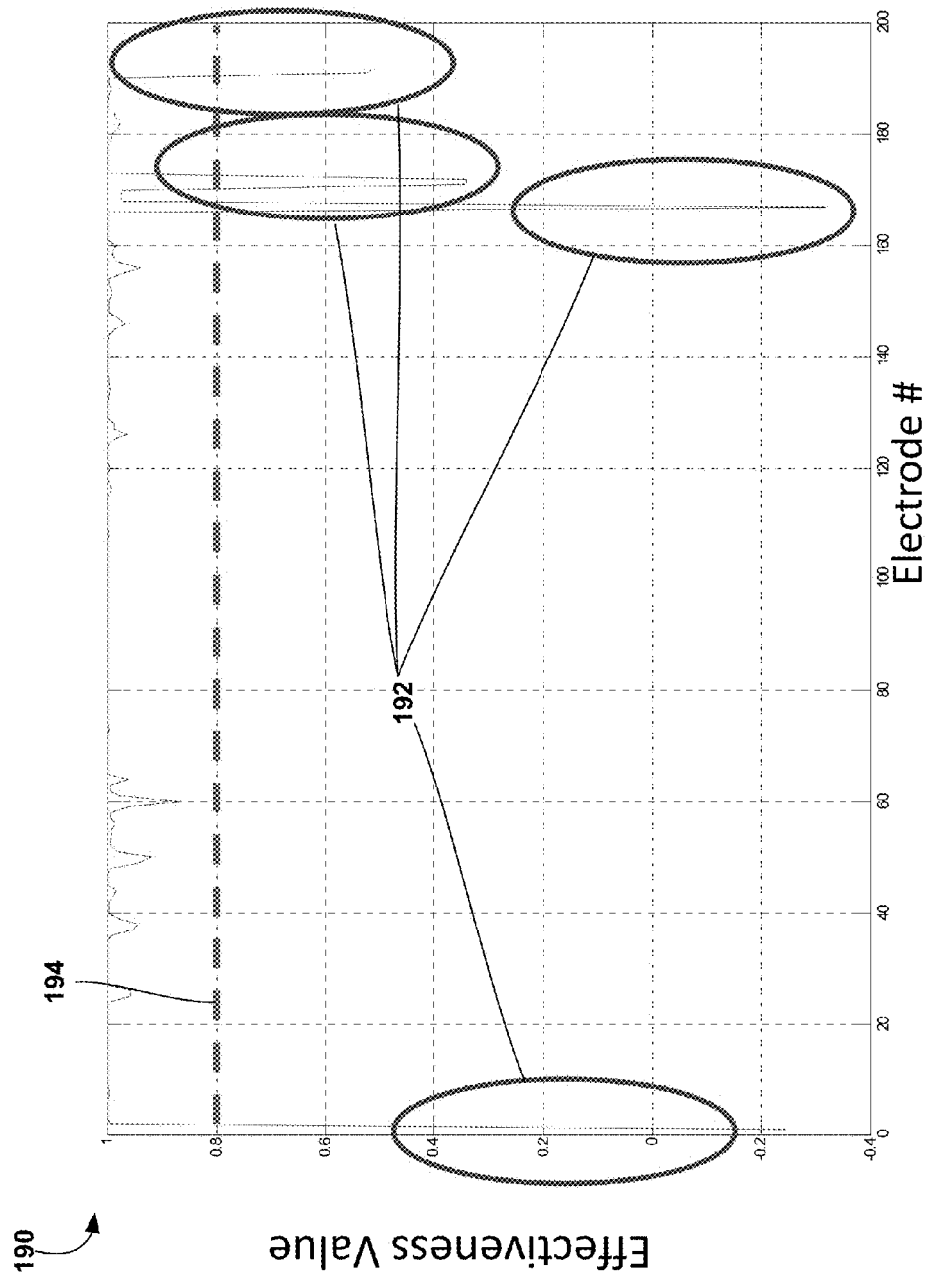
FIG. 10 depicts a graph depicting correlation values for a plurality of electrodes.

A graph 190 depicting effectiveness values for a plurality of electrodes is shown in FIG. 10. The ineffective electrodes 192 are identifiable on the graph 190 as having effectiveness values less than the threshold value 194, which, as shown, is 0.8.

Figure 11:
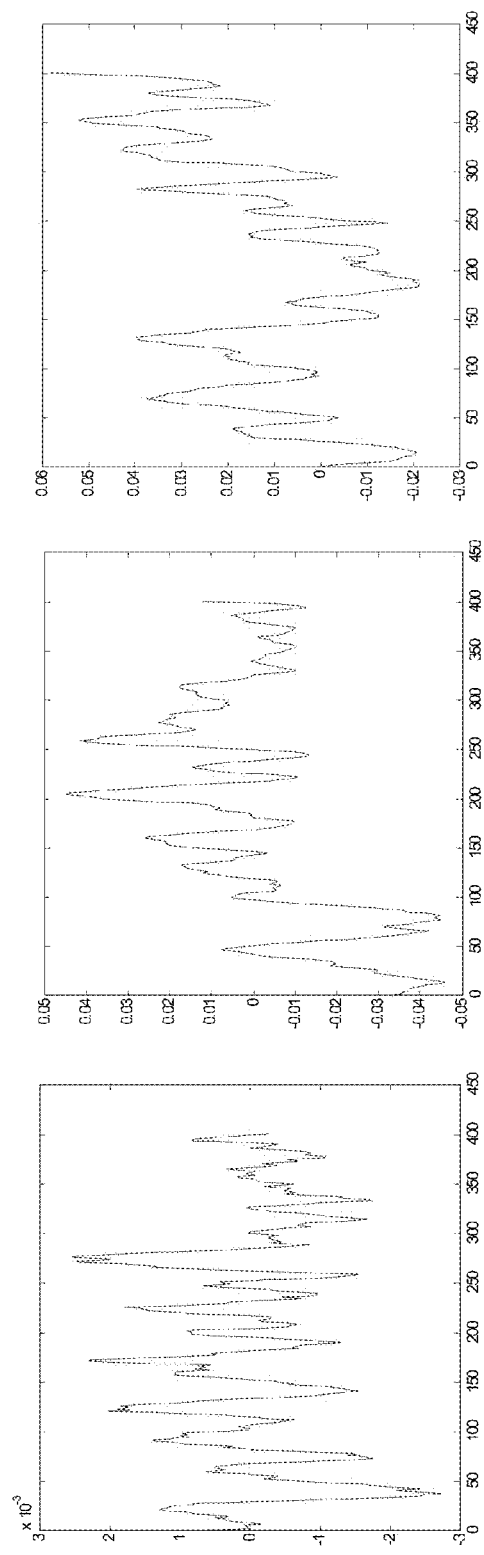
FIG. 11 depicts three graphs depicting signals for ineffective electrodes.
Figure 12:
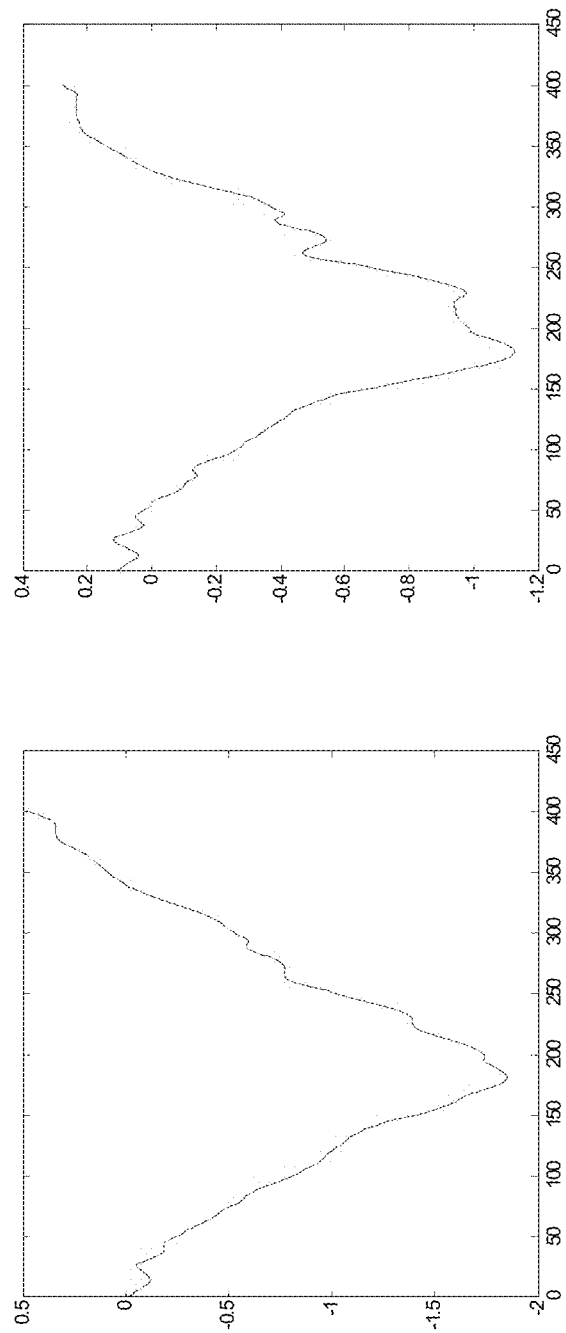
FIG. 12 depicts two graphs depicting signals for effective electrodes.

Cardiac signals measured, or monitored, from ineffective electrodes are depicted in FIG. 11 and cardiac signals measured, or monitored, from effective electrodes are depicted in FIG. 12. As shown, the signals from the ineffective signals appear to not correlate to any pattern or sequence and further appear to depict random noise. The signal from the effective electrodes appears to correlate to a pattern (e.g., a valley) and appear to depict a portion of a valid cardiac signal.

Figure 13:
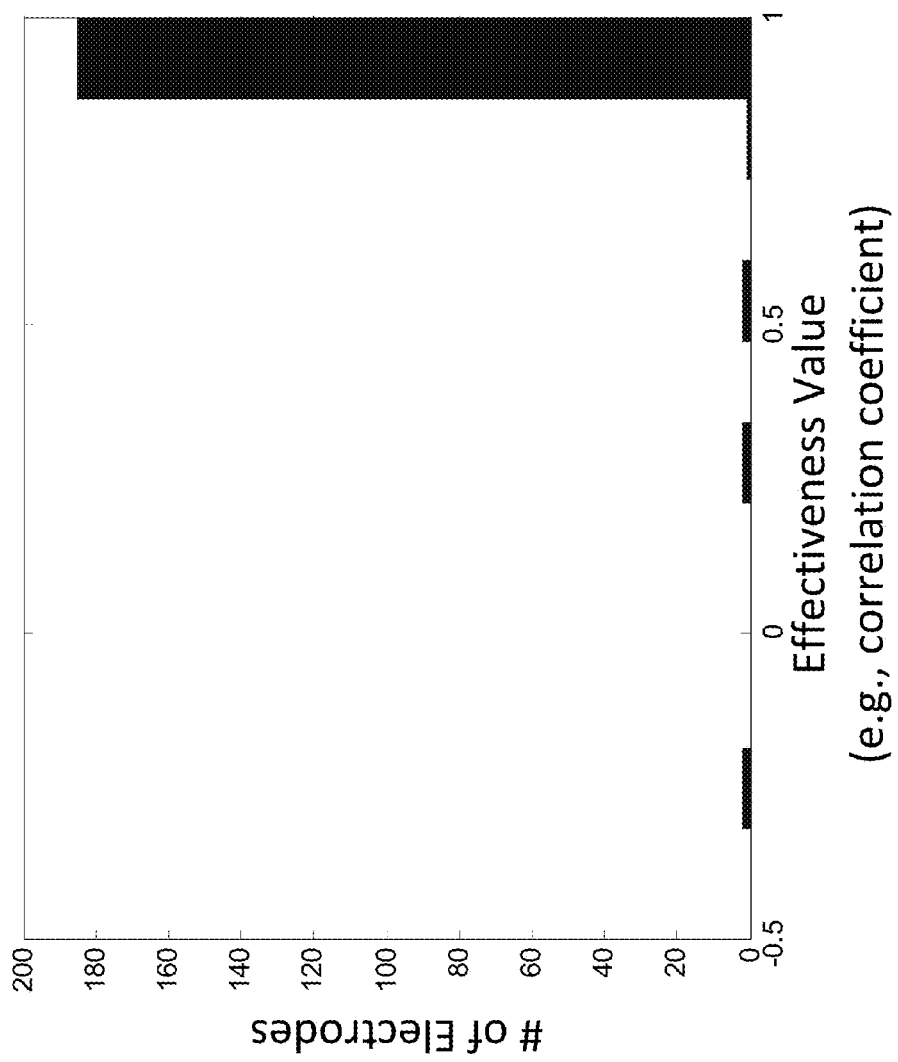
FIG. 13 depicts a graph of a distribution of correlation values for a plurality of electrodes evaluated by, e.g., the exemplary methods of FIGS. 6-7 and 9.

A distribution of correlation values for a plurality of electrodes evaluated by, e.g., the exemplary methods of FIGS. 6-7 and 9, is depicted in FIG. 13. As shown in this example, a vast majority of the electrodes had correlation values between 0.9 and 1.

Figure 14:
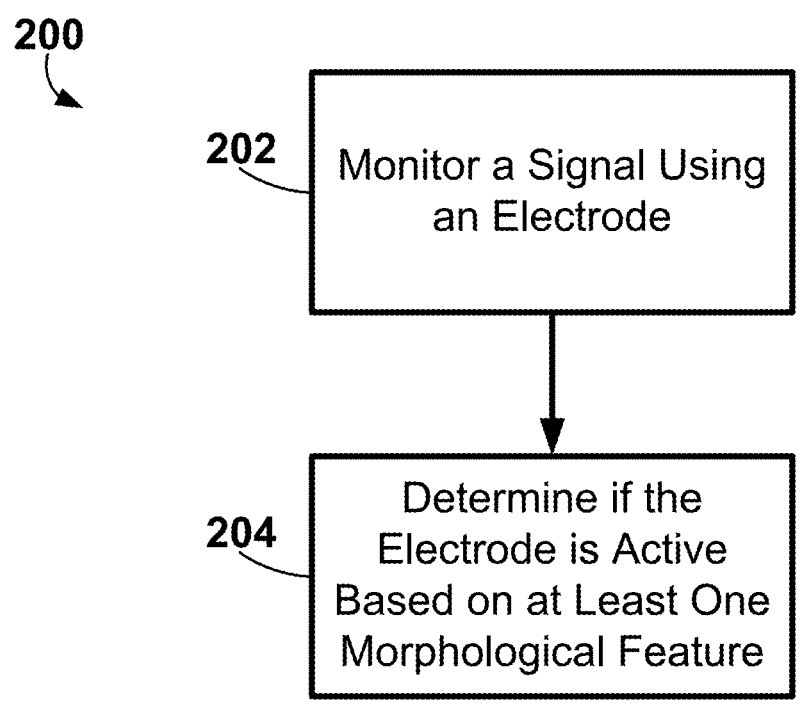
FIG. 14 is a block diagram of an exemplary method of identifying an effective electrode using morphological features.

An exemplary method 200 of identifying an active or effective electrode using morphological features is depicted in FIG. 14. In at least one embodiment, the method 200 may be used prior to the exemplary method 170 described herein with reference to FIG. 9 to, e.g., prevent signals from spatially adjacent electrodes to be compared, or correlated, when one or more of the spatially adjacent electrodes read, or sense, only a flat line or noise. In at least one embodiment, the method 200 may be performed on its own to provide an effectiveness value for an active or effective electrode.

The method 200 includes monitoring a signal using an electrode 202 and analyzing at least one morphological feature of the signal to determine if the electrode is active (or effective) 204. For example, whether an electrode is active or effective may be determined by at least one of the signal maximum value, minimum value, difference between maximum and minimum value, maximum slope, minimum slope, difference between maximum slope and minimum slope, etc. The morphological feature may be compared to a threshold value (e.g., greater than or equal to a predefined value, less than or equal to another predefined value, etc.).

For example, features of the signal from one electrode within a depolarization cycle (e.g., amplitude, slope, etc.) may be used to judge if the value corresponding to those features is within physiologic limits. More specifically, e.g., ECG signal depolarization amplitude value should be within certain physiologic limits such as, e.g., greater than or equal to 0.1 mV and less than or equal to 10 mV. The ECG signal depolarization peak-to-peak amplitude value may be evaluated by comparing the value to the physiological limits to determine if the electrode is active (which, e.g., may be useful if multiple spatially adjacent electrodes are all recording a flat line). Physiologic limits on signal depolarization amplitude for electrode arrays in contact with cardiac tissue may be much larger, e.g., greater than or equal to 1 mV and less than or equal to 50 mV.

These values or data for various electrodes may be mapped (e.g., mapped to a grid for visualization, mapped to a database for analysis, etc.) and/or compared to identify one or more active and/or effective electrodes.

Figure 15:
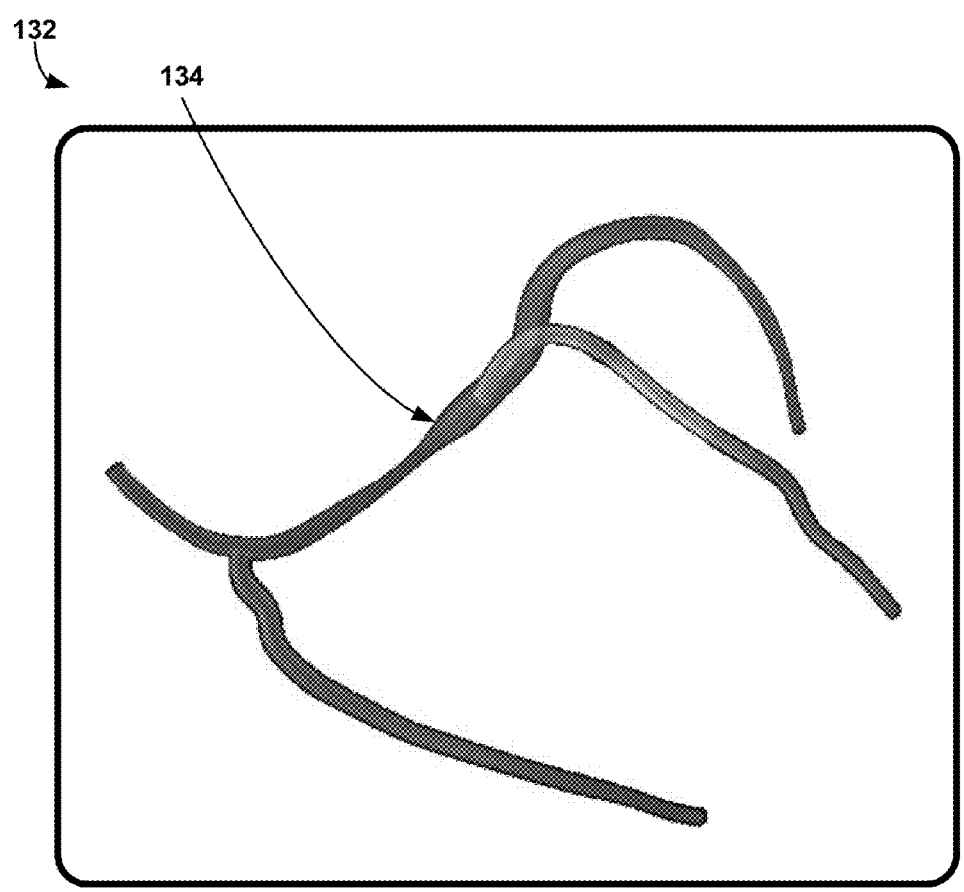
FIG. 15 is an exemplary graphical user interface depicting blood vessel anatomy configured to assist a user in navigating an implantable electrode to a region of a patient's heart for cardiac therapy.

An exemplary graphical user interface 132 including blood vessel anatomy 134 of a patient's heart is shown in FIG. 15 that may be used by a user to navigate an implantable electrode to a region of the patient's heart. The blood vessel anatomy as well as other data such as mechanical motion information, etc. of the heart may be captured using the imaging apparatus 120 described herein, which may be configured to image at least a portion of blood vessel anatomy of the patient's heart and provide image data used by the computing apparatus 140 to provide mechanical motion information or data. The data or information depicted on the blood vessel anatomy of the patient's heart in FIG. 15 may be further monitored, or gathered, using the electrode apparatus 110 described herein.

A user may view and/or use the graphical user interface 132 of FIG. 15 to determine, or identify, one or more candidate site regions of the displayed portion or region of the patient's heart for implantation of implantable electrodes. For example, a user may view mechanical motion information, e.g., grey-scaling or color-coding applied to the blood vessel anatomy in FIG. 15, and identify a candidate site region of the patient's heart based on the mechanical motion information. For example, a user may identify one or more regions having, e.g., mechanical motion times greater than a threshold, having the longest mechanical motion time, etc.

Figure 16:
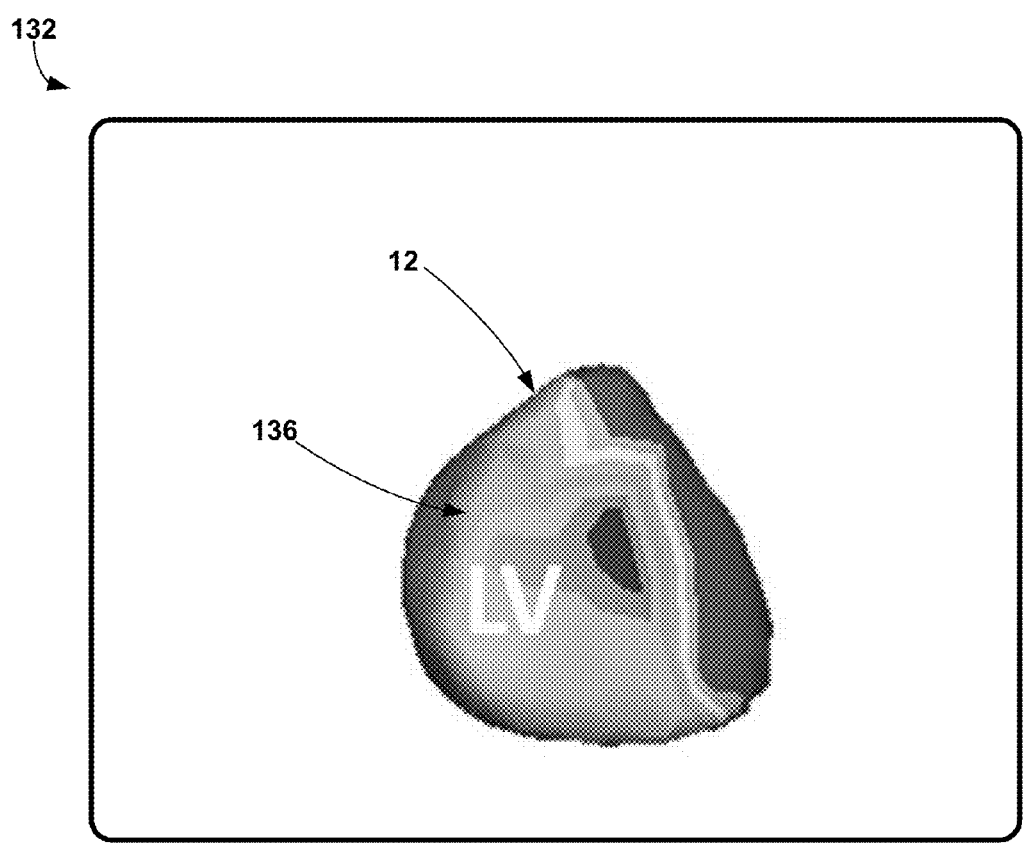
FIG. 16 is an exemplary graphical user interface depicting a human heart including activation times mapped thereon configured to assist a user in navigating an implantable electrode to a region of a patient's heart for cardiac therapy.

Another exemplary graphical user interface 132 including a graphical depiction of a patient's heart 12 is shown in FIG. 16 that may be used by a user to navigate an implantable electrode to a region of the patient's heart. More specifically, a posterior side of a human heart 12 is depicted in the graphical user interface 132 of FIG. 16 with surrogate electrical activation times 136 color-coded, or gray-scaled, across the surface of the heart 12. As used herein, surrogate electrical activation data (e.g., surrogate electrical activation times, surrogate electrical activation time maps, etc.) may be defined as data representative of actual, or local, electrical activation data of one or more regions of the patient's heart. For example, electrical signals measured at the left anterior surface location of a patient's torso may be representative, or surrogates, of electrical signals of the left anterior left ventricle region of the patient's heart, electrical signals measured at the left lateral surface location of a patient's torso may be representative, or surrogates, of electrical signals of the left lateral left ventricle region of the patient's heart, electrical signals measured at the left posterolateral surface location of a patient's torso may be representative, or surrogates, of electrical signals of the posterolateral left ventricle region of the patient's heart, and electrical signals measured at the posterior surface location of a patient's torso may be representative, or surrogates, of electrical signals of the posterior left ventricle region of the patient's heart.

As shown, the posterolateral left ventricle region shows late activation (e.g., about 150 milliseconds). In other embodiments, both a posterior and anterior side of a human heart may be graphically depicted and overlaid with electrical activation information. The data or information depicted on the patient's heart 12 in FIG. 16 may be further monitored, or gathered, using the electrode apparatus 110 described herein.

The techniques described in this disclosure, including those attributed to the IMD 16, the programmer 24, the computing apparatus 140, and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed:

1. A system for use in cardiac therapy comprising:
   electrode apparatus comprising a plurality of electrodes configured to be located proximate tissue of a patient;
   display apparatus comprising a graphical user interface, wherein the graphical user interface is configured to graphically depict at least a portion of anatomy of the patient's heart for use in assisting a user in navigating at least one implantable electrode to a region of the patient's heart; and
   computing apparatus coupled to the electrode apparatus and display apparatus, wherein the computing apparatus is configured to perform an effectiveness test for each electrode of the plurality of electrodes resulting in an effectiveness value for each electrode representative of the effectiveness of the electrode in providing a valid sensing signal from the tissue of the patient, wherein, to perform the effectiveness test for each electrode, the computing apparatus is further configured to:
   monitor a first signal from the patient using a primary electrode being tested,
   monitor at least one secondary signal from the patient using at least one neighbor electrode, wherein the at least one neighbor electrode is spatially adjacent to the primary electrode,
   store a portion of the first signal being monitored using the primary electrode being tested over a time period,
   store a portion of each of the at least one secondary signal being monitored using the at least one neighbor electrode over the time period, compare the portion of the first signal monitored using the primary electrode being tested to the portion of each of the at least one secondary signal to provide at least one effectiveness value representative of the effectiveness of the same primary electrode being tested in providing a valid sensing signal from the tissue of the patient, and display, on the graphical user interface, information for use in assisting a user in at least one of assessing a patient's cardiac health, evaluating and adjusting cardiac therapy delivered to a patient, and navigating at least one implantable electrode to a region of the patient's heart.

2. The system of claim 1, wherein each of the at least one effectiveness value for each primary electrode represent a correlation value between the primary electrode and one neighbor electrode.

3. The system of claim 1, wherein the time period corresponds to ventricular depolarization.

4. The system of claim 1, wherein the time period is less than or equal to 250 milliseconds.

5. The system of claim 1, wherein the at least one neighbor electrode is within 3 centimeters from the primary electrode.

6. The system of claim 1, wherein the effectiveness value comprises a Pearson correlation coefficient.

7. The system of claim 1, wherein the plurality of electrodes comprises surface electrodes positioned in an array.

8. The system of claim 1, wherein the effectiveness value comprises a correlation value, and wherein the computing apparatus is further configured to disable any electrode of the plurality of electrodes having all of their at least one correlation value less than or equal to a selected threshold value.

9. The system of claim 1, wherein the computing apparatus is further configured to perform an additional effectiveness test for each electrode of the plurality of electrodes resulting in at least one additional correlation value for each electrode if more than a selected percentage of the plurality of electrodes had all of their at least one correlation value less than a selected threshold value.

10. The system of claim 1, wherein the computing apparatus is further configured to generate a graphical map comprising the plurality of electrodes spatially distributed and the effectiveness values of the plurality of electrodes.

11. The system of claim 1, wherein information for use in assisting a user in at least one of assessing a patient's cardiac health, evaluating and adjusting cardiac therapy delivered to a patient, and navigating at least one implantable electrode to a region of the patient's heart comprises at least a portion of the blood vessel anatomy of the patient's heart.

12. A method for use in cardiac therapy comprising:
monitoring a first signal from a patient using a primary electrode being tested to determine an effectiveness of the primary electrode in providing a valid sensing signal from tissue of the patient;
monitoring at least one secondary signal from the patient using at least one neighbor electrode, wherein the at least one neighbor electrode is spatially adjacent to the primary electrode;
storing a portion of the first signal being monitored using the primary electrode being tested over a time period;
storing a portion of each of the at least one secondary signal being monitored using the at least one neighbor electrode over the time period;
comparing the portion of the first signal monitored using the primary electrode being tested to the portion of each of the at least one secondary signal to provide at least one effectiveness value representative of the effectiveness of the same primary electrode being tested in providing a valid sensing signal for sensing cardiac signals from the tissue of the patient; and displaying, on a graphical user interface, information for use in at least one of assessing a patient's cardiac health, evaluating and adjusting cardiac therapy delivered to a patient, and assisting a user in navigating at least one implantable electrode to a region of the patient's heart.

13. The method of claim 12, wherein each of the at least one effectiveness value for each primary electrode represent a correlation value between the primary electrode and one neighbor electrode.

14. The method of claim 12, wherein the time period corresponds to ventricular depolarization.

15. The method of claim 12, wherein the at least one neighbor electrode is within 3 centimeters from the primary electrode.

16. The method of claim 12, wherein the plurality of electrodes comprises surface electrodes positioned in an array.

17. The method of claim 12, wherein the effectiveness value comprises a correlation value, and wherein the method further comprises disabling any electrode of the plurality of electrodes having all of their at least one correlation value less than or equal to a selected threshold value.

18. The method of claim 12, wherein the method further comprises performing an additional effectiveness test for each electrode of the plurality of electrodes resulting in at least one additional correlation value for each electrode if more than a selected percentage of the plurality of electrodes had all of their at least one correlation value less than a selected threshold value.

19. The method of claim 12, wherein the method further comprises generating a graphical map comprising the plurality of electrodes spatially distributed and the effectiveness values of the plurality of electrodes.

20. A system for use in cardiac therapy comprising:
electrode means for monitoring a first signal from a patient using a primary electrode being tested to determine the effectiveness of the primary electrode in providing a valid sensing signal from tissue of the patient and for monitoring at least one secondary signal from the patient using at least one neighbor electrode, wherein the at least one neighbor electrode is spatially adjacent to the primary electrode;
computing means for storing a portion of the first signal being monitored using the primary electrode being tested over a time period, for storing a portion of each of the at least one secondary signal being monitored using the at least one neighbor electrode over the time period, and for comparing the portion of the first signal monitored using the primary electrode being tested to the portion of each of the at least one secondary signal to provide at least one effectiveness value representative of the effectiveness of the same primary electrode being tested in providing a valid sensing signal from the tissue of the patient; and
display means for displaying, on a graphical user interface, information for use in at least one of assessing a patient's cardiac health, evaluating and adjusting cardiac therapy delivered to a patient, and assisting a user in navigating at least one implantable electrode to a region of the patient's heart.

\* \* \* \* \*